US009739695B2

(12) United States Patent
Michishita et al.

(10) Patent No.: US 9,739,695 B2
(45) Date of Patent: Aug. 22, 2017

(54) WATER JET PEENING COMPRESSIVE RESIDUAL STRESS TEST METHOD, TEST DEVICE, AND TEST FACILITY

(71) Applicant: MITSUBISHI HEAVY INDUSTRIES, LTD., Tokyo (JP)

(72) Inventors: Yukio Michishita, Tokyo (JP); Takahiro Ota, Tokyo (JP); Nobuyuki Hori, Tokyo (JP)

(73) Assignee: MITSUBISHI HEAVY INDUSTRIES, LTD., Tokyo (JP)

(*) Notice: Subject to any disclaimer, the term of this patent is extended or adjusted under 35 U.S.C. 154(b) by 98 days.

(21) Appl. No.: 14/766,559

(22) PCT Filed: Feb. 10, 2014

(86) PCT No.: PCT/JP2014/053033

§ 371 (c)(1),
(2) Date: Aug. 7, 2015

(87) PCT Pub. No.: WO2014/126039

PCT Pub. Date: Aug. 21, 2014

(65) Prior Publication Data

US 2015/0377756 A1 Dec. 31, 2015

(30) Foreign Application Priority Data

Feb. 12, 2013 (JP) ................................ 2013-024515

(51) Int. Cl.
*G21C 17/01* (2006.01)
*G01N 3/10* (2006.01)
(Continued)

(52) U.S. Cl.
CPC .............. *G01N 3/10* (2013.01); *G01L 5/0052* (2013.01); *G21C 17/001* (2013.01); *G21C 17/01* (2013.01);
(Continued)

(58) Field of Classification Search
CPC .... G21C 17/001; G21C 17/01; G21C 19/207; G21C 19/28; G01N 3/10; G01N 3/06;
(Continued)

(56) References Cited

U.S. PATENT DOCUMENTS 2,607,213 A 8/1952 Barton et al.
3,695,091 A * 10/1972 Smith ...................... B24C 1/10 72/53

(Continued)

FOREIGN PATENT DOCUMENTS

JP 5-195052 A 8/1993
JP 6-79626 A 3/1994

(Continued)

OTHER PUBLICATIONS

Official Communication under Rule 71(3) EPC dated Oct. 7, 2016, issued in counterpart European Patent Application No. 14 751 143.0. (7 pages).

(Continued)

*Primary Examiner* — Blake A Tankersley
(74) *Attorney, Agent, or Firm* — Westerman, Hattori, Daniels & Adrian, LLP

(57) ABSTRACT

A plastically deformable almen strip is held under a predetermined underwater environment in which water jet peening is carried out, and a result of providing compressive residual stress in the water jet peening is confirmed by jetting water jet to the almen strip.

9 Claims, 16 Drawing Sheets

(51) Int. Cl.
*G21C 17/00* (2006.01)
*G01L 5/00* (2006.01)
*B23P 9/04* (2006.01)
*G21C 19/20* (2006.01)
*G21C 19/28* (2006.01)
*C21D 7/06* (2006.01)

(52) U.S. Cl.
CPC .................. *B23P 9/04* (2013.01); *C21D 7/06* (2013.01); *G21C 19/207* (2013.01); *G21C 19/28* (2013.01)

(58) Field of Classification Search
CPC G01N 2203/0664; G01L 5/0052; C21D 7/06; C21D 7/04; B23P 9/04; C22F 1/00; B24C 1/10
See application file for complete search history.

(56) References Cited

U.S. PATENT DOCUMENTS 4,102,176 A 7/1978 Fuchs
5,305,361 A 4/1994 Enomoto et al.
6,855,208 B1 * 2/2005 Soyama .................... B24C 1/10 134/1
2012/0199506 A1 8/2012 Beach et al.

FOREIGN PATENT DOCUMENTS

JP 2000-263337 A 9/2000
JP 2003-206995 A 7/2003
JP 2004-42154 A 2/2004
JP 2004-45115 A 2/2004
JP 2006-201141 A 8/2006
JP 2012-240099 A 12/2012

OTHER PUBLICATIONS

Translation of Written Opinion dated Mar. 18, 2014, issued in counterpart application No. PCT/JP2014/053033 (9 pages).
International Search Report dated Mar. 18, 2014, issued in counterpart International Application No. PCT/JP2014/053033 (4 pages).
Written Opinion of the International Searching Authority dated Mar. 18, 2014, issued in counterpart International Application No. PCT/JP2014/053033 (5 pages).
Soyama et al., "An Evaluation of Cavitation Shotless Peening by Using Almen Strip", The Japan Society of Mechanical Engineers Tohoku Shibu Dai 36-ki Sokai Koenkai Koen Ronbunshu, Mar. 10, 2001, pp. 164-165, No. 011-1.
Odhiambo, Dan et al., "Cavitation shotless peening for improvement of fatigue strength of carbonized steel", International Journal of Fatigue, vol. 25, No. 9-11, Sep. 2003, pp. 1217-1222, dated Dec. 17, 2015.
Extended European Search Report dated Dec. 17, 2015, issued in counterpart European Application No. 14751143.0 (8 pages).
Office Action dated Mar. 7, 2017, issued in counterpart Japanese Patent Application No. 2013-024515, with English translation. (4 pages).
Office Action dated Dec. 20, 2016, issued in counterpart Japanese Application No. 2013-024515, with English translation (9 pages).

* cited by examiner 4
43f
40
40a
40f
40e
2b
40b
40d
40c
40h
43e
43d
43a
43c
43
43h
42
45
43g
43e
40h
43b
163b
43b 4
43
43f
40g
40f
40
40a
43e
40h
40h
43d
43a
43a
43c
43b
43b
43g
43h
43b
43b
40h
40h
45
42
43e
40b
40d

WATER JET PEENING COMPRESSIVE RESIDUAL STRESS TEST METHOD, TEST DEVICE, AND TEST FACILITY

FIELD

The present invention relates to a method of testing compressive residual stress in water jet peening, a test device, and a test facility.

BACKGROUND

For example, an atomic power plant including a pressurized water reactor (PWR) uses light water that is primary cooling water, as a reactor coolant and a neutron moderator, keeps the light water as high-temperature and high-pressure water that does not boil throughout an entire reactor internal, sends the high-temperature and high-pressure water to a steam generator to generate steam by heat exchange, and sends the steam to a turbine generator to generate power.

In such an atomic power plant, the pressurized water reactor needs to have periodic checks of various structures in order to secure sufficient safety and reliability. Then, when the checks are conducted and failure is found, a necessary place related to the failure is repaired. For example, in the pressurized water reactor, a reactor vessel main body is provided with a large number of instrumentation nozzles that penetrate a lower mirror. In each of the instrumentation nozzles, an in-core instrumentation guide tube is fixed to an in-core side upper end portion, and a conduit tube is connected to an ex-core side lower end portion. Further, a neutron flux detector that can measure a neutron flux can be inserted from the instrumentation nozzle to a reactor internal (fuel assembly) through the in-core instrumentation guide tube with the conduit tube. Further, the reactor vessel main body is provided with an output-side nozzle for supplying the primary cooling water to the steam generator, and an inlet-side nozzle for taking in the primary cooling water subjected to the heat exchange in the steam generator. A primary cooling water pipe, which communicates into the steam generator, is connected with these nozzles by welding. Since materials of the nozzles and the primary cooling water pipe are different, a safe end pipe is connected between the nozzles and the primary cooling water pipe by welding.

The instrumentation nozzle is configured such that an in-core instrumentation cylinder is fit into a mounting hole of the reactor vessel main body and is welded. Therefore, tensile stress may remain in the in-core instrumentation cylinder, a welded portion of the in-core instrumentation cylinder, and its peripheral portions, and a probability of occurrence of stress corrosion cracking becomes high due to long-term use. Further, tensile residual stress caused in the welded portion and its peripheral portion may also be a cause of the stress corrosion cracking in the inlet-side nozzle and the outlet-side nozzle. Therefore, conventionally, there is a water jet peening technology, in which tensile residual stress on a surface is improved into compressive residual stress, so that the stress corrosion cracking is prevented. The water jet peening is to jet high-pressure water containing cavitation bubbles to a surface of a metal member in water to improve the tensile residual stress on the surface of the metal member into the compressive residual stress. For example, Patent Literature 1 below discloses a technology that performs the water jet peening for the instrumentation nozzles.

CITATION LIST

Patent Literature

Patent Literature 1: Japanese Laid-open patent Publication No. 2006-201141

SUMMARY

Technical Problem

By the way, in the above-described water jet peening, confirmation of a result of providing the compressive residual stress is desired. Although an almen strip and a holding tool of the almen strip are described in JIS B 2711 regarding shot peening. However, there is no description about the water jet peening.

The present invention solves the above-described problem, and an objective is to provide a water jet peening compressive residual stress test method, a test device, and a test facility, which enable confirmation of the degree and the size of a result of providing compressive residual stress in water jet peening.

Solution to Problem

According to an aspect of the present invention, a water jet peening compressive residual stress test method includes: holding a plastically deformable almen strip under a predetermined underwater environment; and jetting water jet to the almen strip.

According to the water jet peening compressive residual stress test method, the degree and the size of a result of providing compressive residual stress in water jet peening can be confirmed.

Advantageously, the water jet peening compressive residual stress test method includes: providing the underwater environment by putting water in a sealed water tank and pressurizing the sealed water tank; holding the almen strip under the underwater environment; and jetting the water jet to the almen strip.

According to the water jet peening compressive residual stress test method, an actual underwater environment in which the water jet peening is carried out can be simulated, and confirmation accuracy of the degree and the size of a result of providing compressive residual stress in water jet peening can be improved.

According to another aspect of the present invention, a water jet peening compressive residual stress test device includes: a jet port mounting portion to which a jet port is mounted, the jet port jetting water jet; a high-pressure water pipe mounting portion provided communicating into the jet port mounting portion, and to which a high-pressure water supply pipe is mounted, the high-pressure water supply pipe supplying high-pressure water; and an almen strip holding portion including a support surface facing the jet port mounting portion, and an attaching portion configured to allow a plate surface of a plastically deformable plate-like almen strip to be in contact with and attached to the support surface.

According to the water jet peening compressive residual stress test device, the water jet is jetted to the almen strip held in the almen strip holding portion through the jet port under the underwater environment, so that water jet peening is applied, and the almen strip is plastically deformed. Then, the plastic deformation of the almen strip is measured, so that the degree and the size of a result of providing compressive residual stress provided in the water jet peening can be confirmed.

Advantageously, in the water jet peening compressive residual stress test device, the attaching portion includes a pressing member including a through hole through which a portion of the almen strip is let out, the portion being jetted the water jet, and a pressing surface configured to abut on an outer edge of the almen strip, and a fixing member configured to fix the pressing member to sandwich the almen strip between the pressing surface of the pressing member and the support surface.

According to the water jet peening compressive residual stress test device, the water jet peening is applied to the portion of the almen strip, the portion being let out through the through hole. When the water jet is jetted to the almen strip, an inflow of the water jet to a portion not let out through the through hole and the portion between the almen strip and the support surface can be suppressed with the through hole. As a result, the plastic deformation of the almen strip by an action other than the water jet peening can be suppressed, and more highly accurate evaluation of compressive residual stress provided in the water jet peening can be provided.

Advantageously, in the water jet peening compressive residual stress test device, a recessed portion configured to allow the almen strip to be inserted to surround a vicinity of the almen strip is included in at least one of the support surface and the pressing surface.

According to the water jet peening compressive residual stress test device, when the water jet is jetted to the almen strip, an inflow of the water jet to between the almen strip and the support surface is further suppressed with a step of an outer periphery of the recessed portion. Therefore, deformation of the almen strip due to the inflow of the water jet to between the almen strip and the support surface can be further suppressed. As a result, the plastic deformation of the almen strip by an action other than the water jet peening can be suppressed, and more highly accurate evaluation of compressive residual stress provided in the water jet peening can be performed.

Advantageously, in the water jet peening compressive residual stress test device, the support surface has an area broader than an effective range where the water jet acts, and the attaching portion allows the almen strip to be attached, spacing an area broader than the effective range.

According to the water jet peening compressive residual stress test device, the almen strip with the area broader than the effective range can be held, and the water jet peening is applied to a portion of the almen strip in the effective range. Therefore, when the water jet is jetted to the almen strip, the inflow of the water jet to between the almen strip and the support surface can be suppressed. As a result, the plastic deformation of the almen strip by an action other than the water jet peening can be suppressed, and more highly accurate evaluation of compressive residual stress provided in the water jet peening can be performed.

Advantageously, in the water jet peening compressive residual stress test device, includes: a test piece holding portion provided in parallel to the almen strip holding portion, and configured to hold a residual stress measurement test piece that causes residual stress.

According to the water jet peening compressive residual stress test device, the degree and the size of a result of providing compressive residual stress provided in the water jet peening can be confirmed by comparison of the almen strip and the residual stress measurement test piece.

Advantageously, in the water jet peening compressive residual stress test device, includes: a block portion configured to block a space between the almen strip holding portion and the jet port mounting portion; and an opening/closing mechanism configured to move the block portion to open/close the space between the almen strip holding portion and the jet port mounting portion.

According to the water jet peening compressive residual stress test device, the space between the almen strip holding portion and the jet port mounting portion is blocked and jetting of the water jet to the almen strip is controlled until when the water jet jetted through the jet port is stabilized to a jet condition in which the water jet peening is carried out, and the space between the almen strip holding portion and the jet port mounting portion is released and the water jet is jetted to the almen strip after the jet condition is stabilized. As a result, the almen strip is plastically deformed in the stable jet condition. Therefore, more highly accurate evaluation of compressive residual stress provided in the water jet peening can be performed.

Advantageously, in the water jet peening compressive residual stress test device includes a slide-moving mechanism configured to slide and move the jet port mounting portion and the high-pressure water pipe mounting portion in a direction perpendicular to a direction into which the jet port mounted to the jet port mounting portion faces.

According to the water jet peening compressive residual stress test device, the jet port is retracted from a position above the almen strip holding portion (almen strip) until the water jet jetted through the jet port is stabilized to a jet condition in which the water jet peening is carried out, and the jet port is moved to the position above the almen strip holding portion (almen strip) and the water jet is jetted to the almen strip after the jet condition is stabilized. As a result, the almen strip is plastically deformed in the stable jet condition. Therefore, more highly accurate evaluation of compressive residual stress provided in the water jet peening can be performed.

According to still another aspect of the present invention, a water jet peening compressive residual stress test facility includes: a water tank configured to form a predetermined underwater environment; and a high-pressure water pump configured to send high-pressure water to a high-pressure water supply pipe that supplies the high-pressure water. Any one of the above described water jet peening compressive residual stress test device is arranged under the underwater environment of the water tank, the high-pressure water supply pipe is connected to the water jet peening compressive residual stress test device and the high-pressure water pump, and a water jet peening compressive residual stress test is performed.

According to the water jet peening compressive residual stress test facility, the degree and the size of a result of providing compressive residual stress in the water jet peening can be confirmed.

Advantageously, in the water jet peening compressive residual stress test facility includes: a sealing means configured to seal an inside of the water tank; and a pressurizing means configured to pressurize the inside of the sealed water tank.

According to the water jet peening compressive residual stress test facility, an actual underwater environment in which the water jet peening is carried out can be simulated, and confirmation accuracy of the degree and the size of a result of providing compressive residual stress in the water jet peening can be improved.

Advantageous Effects of Invention

According to the present invention, the degree and the size of a result of providing compressive residual stress in water jet peening can be confirmed.

DESCRIPTION OF EMBODIMENTS

Hereinafter, embodiments according to the present invention will be described in detail based on the drawings. Note that the invention is not limited by these embodiments. Further, configuration elements in the embodiments below include those easy and replaceable by a person skilled in the art, and substantially the same.

Figure 1:
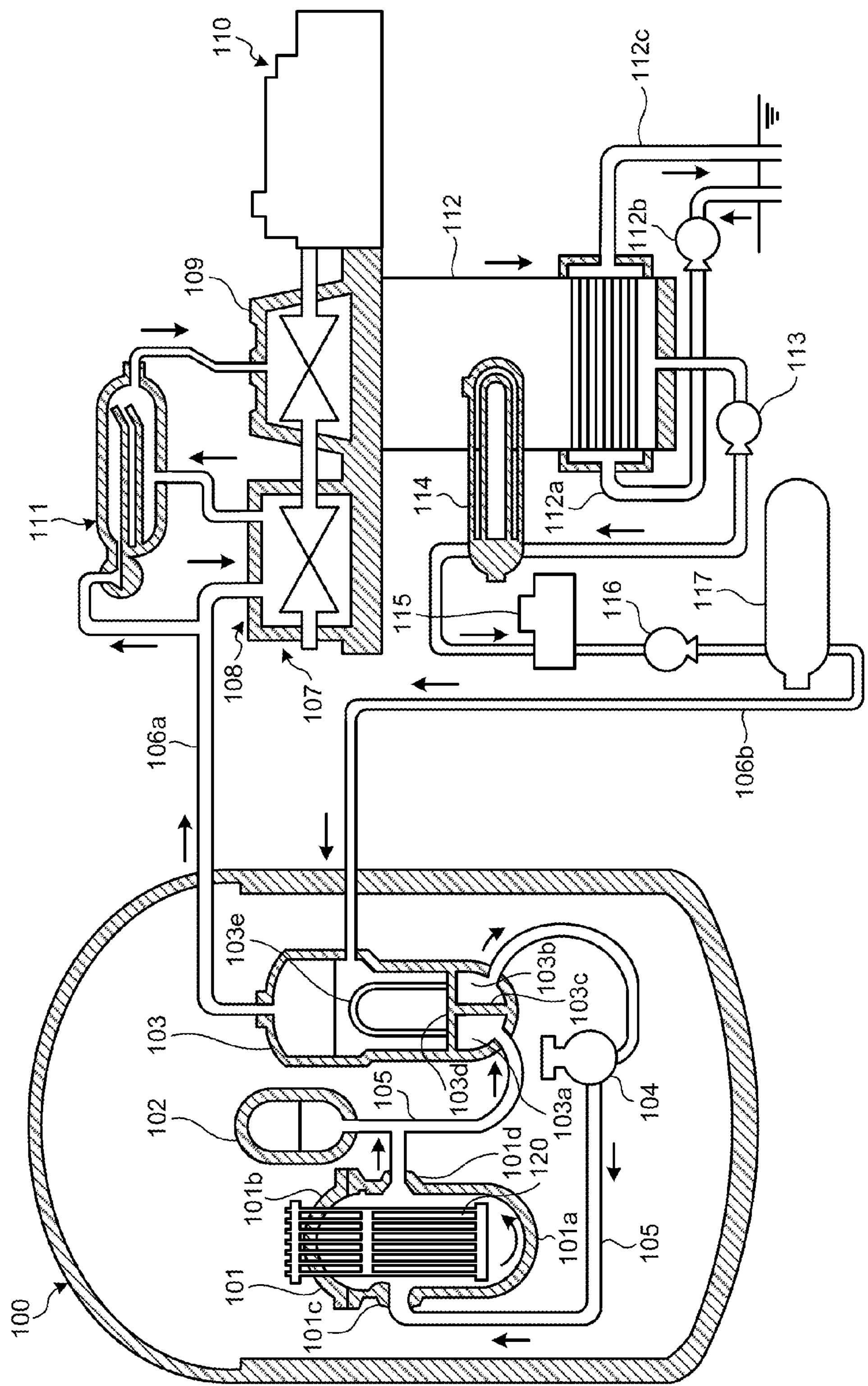
FIG. 1 is a schematic configuration diagram of an example of an atomic power plant.
Figure 2:
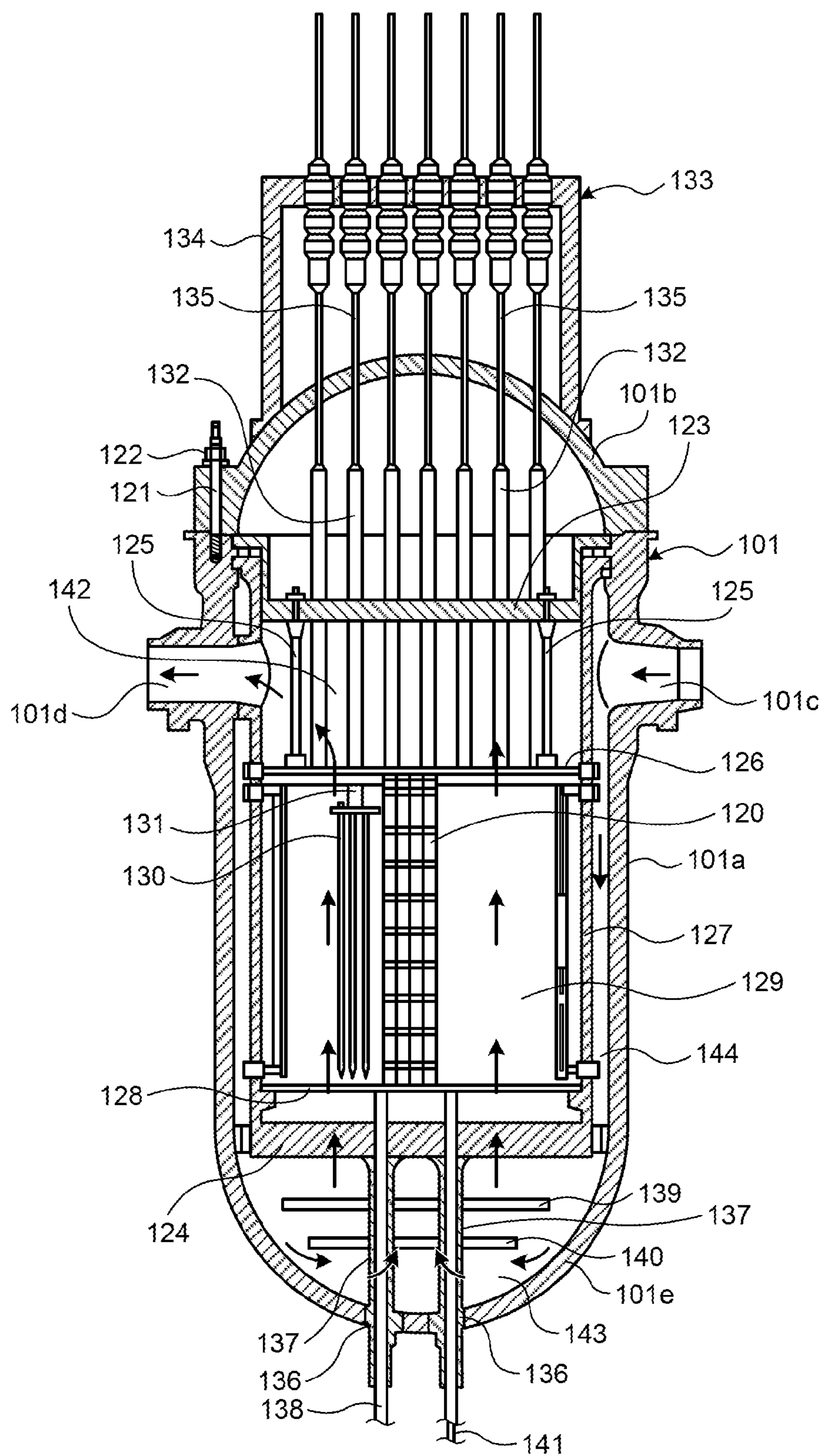
FIG. 2 is a longitudinal sectional view of a pressurized water reactor.
Figure 3:
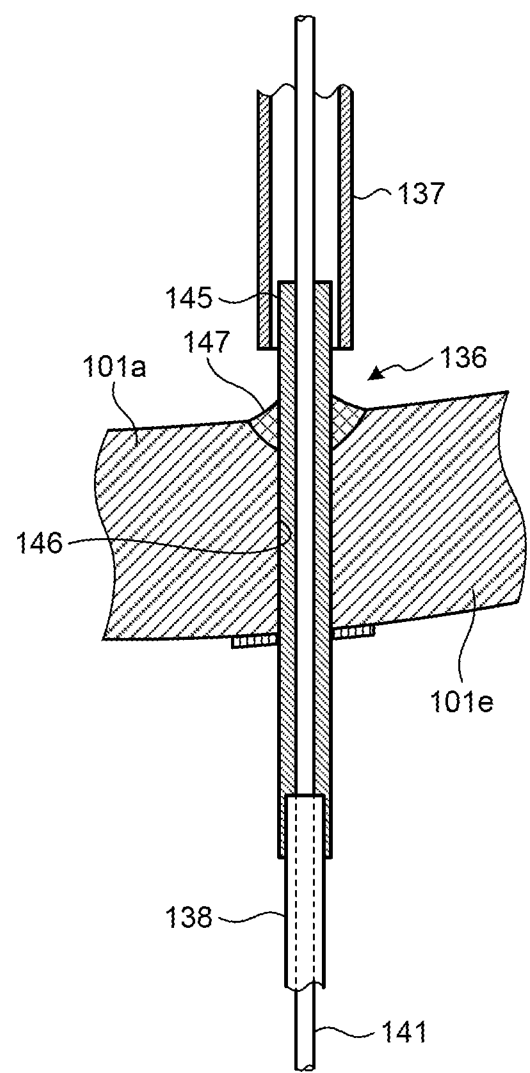
FIG. 3 is a sectional view of an instrumentation nozzle of a reactor vessel.

FIG. 1 is a schematic configuration diagram of an example of an atomic power plant. FIG. 2 is a longitudinal sectional view of a pressurized water reactor. FIG. 3 is a sectional view of an instrumentation nozzle of a reactor vessel.

An atomic power plant illustrated in FIG. 1 includes a pressurized water reactor (PWR). In a containment 100 of the atomic power plant, a reactor vessel 101, a pressurizer 102, a steam generator 103, and a primary cooling water pump 104 of the pressurized water reactor are sequentially connected with a primary cooling water pipe 105, so that a circulation path of primary cooling water is configured.

The reactor vessel 101 stores a fuel assembly 120 therein in a sealed state, and is configured from a reactor vessel main body **101*a* and a reactor vessel cover 101*b* mounted thereon so that the fuel assembly 120 can be inserted/pulled out. The reactor vessel main body 101*a* is provided with an inlet-side nozzle 101*c* and an outlet-side nozzle 101*d* in upper portions, the inlet-side nozzle 101*c* and the outlet-side nozzle 101*d* supplying/discharging light water as primary cooling water. The outlet-side nozzle 101*d* is connected with a primary cooling water pipe 105 to communicate into an inlet-side water chamber 103*a* of the steam generator 103. The inlet-side nozzle 101*c* is connected with the primary cooling water pipe 105 to communicate into an outlet-side water chamber 103*b* of the steam generator 103**.

The inlet-side water chamber **103*a* and the outlet-side water chamber 103*b* are divided with a partition plate 103*c* in a lower portion of the steam generator 103, the lower portion being formed into a semispherical shape. The inlet-side water chamber 103*a* and the outlet-side water chamber 103*b* are divided from an upper portion side of the steam generator 103 with a tube plate 103*d* provided on a ceiling portion. An inverted U-shaped heat transfer pipe 103*e* is provided in the upper portion side of the steam generator 103. End portions of the heat transfer pipe 103*e* are supported by the tube plate 103*d* to connect the inlet-side water chamber 103*a* and the outlet-side water chamber 103*b*. Further, the inlet-side water chamber 103*a* is connected with the inlet-side primary cooling water pipe 105, and the outlet-side water chamber 103*b* is connected with the outlet-side primary cooling water pipe 105. Further, the steam generator 103 is connected with an outlet-side secondary cooling water pipe 106*a* at an upper end of the upper portion side divided with the tube plate 103*d*, and with an inlet-side secondary cooling water pipe 106*b*** at a side portion of the upper portion side.

Further, in the atomic power plant, the steam generator 103 is connected with a steam turbine 107 outside the containment 100 through the secondary cooling water pipes **106*a* and 106*b***, so that a circulation path of the secondary cooling water is configured.

The steam turbine 107 includes a high-pressure turbine 108 and a low-pressure turbine 109, and is connected with a generator 110. Further, a moisture separator and reheater 111 branches from the secondary cooling water pipe **106*a* and is connected with the high-pressure turbine 108 and the low-pressure turbine 109. Further, the low-pressure turbine 109 is connected with a condenser 112. The condenser 112 is connected with the secondary cooling water pipe 106*b*. The secondary cooling water pipe 106*b* is connected with the steam generator 103, as described above, and is provided with a condensate pump 113, a low-pressure feed water heater 114, a deaerator 115, a main feed water pump 116, and a high-pressure feed water heater 117 from the condenser 112 to the steam generator 103**.

Therefore, in the atomic power plant, the primary cooling water is heated in the reactor vessel 101, becomes high temperature and high pressure, is pressurized in the pressurizer 102 to maintain the pressure constant, and is supplied to the steam generator 103 through the primary cooling water pipe 105. In the steam generator 103, heat exchange between the primary cooling water and the secondary cooling water is performed, so that the secondary cooling water is evaporated and becomes steam. The cooled primary cooling water after the heat exchange is collected in the primary cooling water pump 104 side through the primary cooling water pipe 105, and is returned to the reactor vessel 101. Meanwhile, the secondary cooling water that has become the steam by the heat exchange is supplied to the steam turbine 107. According to the steam turbine 107, the moisture separator and reheater 111 removes moisture from exhaust from the high-pressure turbine 108, reheats the steam to cause it in an overheated state, and then sends the steam to the low-pressure turbine 109. The steam turbine 107 is driven by the steam of the secondary cooling water, and the power thereof is transmitted to the generator 110 and electricity is generated. The steam supplied to the driving of the turbine is discharged to the condenser 112. The condenser 112 exchanges heat between cooling water (for example, sea water) taken with a pump 112*b* through an intake pike 112*a* and the steam discharged from the low-pressure turbine 109, and condenses the steam to return the steam to a low-pressure saturated liquid. The cooling water used for the heat exchange is discharged through a drain pipe 112*c*. Further, the condensed saturated liquid becomes the secondary cooling water, and is sent to an outside of the condenser 112 by the condensate pump 113 through the secondary cooling water pipe 106*b*. Further, the secondary cooling water that has passed through the secondary cooling water pipe 106*b* is heated in the low-pressure feed water heater 114 with low-pressure steam bled from the low-pressure turbine 109, for example, impurities such as dissolved oxygen or a non-condensable gas (ammonia gas) in the secondary cooling water are removed in the deaerator 115. Then, the secondary cooling water is sent by the main feed water pump 116, and is heated in the high-pressure feed water heater 117 with high-pressure steam bled from the high-pressure turbine 108, for example, and is then returned to the steam generator 103.

In the pressurized water reactor of the atomic power plant configured as described above, as illustrated in FIG. 2, the reactor vessel cover 101*b* is fixed to the reactor vessel main body 101*a* with a plurality of stud bolts 121 and buts 122 in an openable/closable manner so that the reactor vessel 101 can allow an in-core structure including the fuel assembly 120 to be inserted therein.

An upper portion of the reactor vessel main body 101*a* can open by removal of the reactor vessel cover 101*b*, and a lower portion has a cylindrical shape blocked with a lower mirror 101*e* having a semispherical shape. An upper core support 123 is fixed above the inlet-side nozzle 101*c* and the outlet-side nozzle 101*d*, and a lower core support 124 is fixed to a position near the lower mirror 101*e*, inside the reactor vessel main body 101*a*. The upper core support 123 and the lower core support 124 form a disk-like shape, and a large number of flow holes (not illustrated) is formed in the upper core support 123 and the lower core support 124. Then, the upper core support 123 is connected with an upper core plate 126 in which a large number of flow holes (not illustrated) is formed, through a plurality of core support rods 125.

A core barrel 127 that forms a cylindrical shape is arranged with a predetermined gap with an inner wall surface in the reactor vessel main body 101*a*. An upper portion of the core barrel 127 is connected with the upper core plate 126, and a lower portion is connected with a lower core support plate 128 that forms a disk-like shape and in which a large number of flow holes (not illustrated) is formed. Then, the lower core support plate 128 is supported by the lower core support 124. That is, the core barrel 127 is supported by the lower core support 124 of the reactor vessel main body 101*a*.

A reactor internal 129 is formed of the upper core plate 126, the core barrel 127, and the lower core support plate 128, and a large number of fuel assemblies 120 is arranged in the reactor internal 129. The fuel assembly 120 is configured such that, although not illustrated, a large number of fuel rods are bundled with a support grid in a grid-like manner, and an upper nozzle is fixed to an upper end portion, and a lower nozzle is fixed to a lower end portion. Further, a large number of control rods 130 are arranged in the reactor internal 129. Upper end portions of the large number of control rods 130 are put together, and serve as a control rod cluster 131, and can be inserted into the fuel assemblies 120. A larger number of control rod cluster guide tubes 132 are fixed to the upper core support 123 by penetrating the upper core support 123, and lower end portions of the control rod cluster guide tubes 132 are extended to the control rod cluster 131 in the fuel assemblies 120.

An upper portion of the reactor vessel cover 101*b* that configures the reactor vessel 101 forms a semispherical shape, and the reactor vessel cover 101*b* is provided with a control rod driving mechanism 133 of a magnetic jack that is housed in a housing 134 integrally formed with the reactor vessel cover 101*b*. Upper end portions of the large number of control rod cluster guide tubes 132 are extended to the control rod driving mechanism 133, and control rod cluster drive shafts 135 are extended from the control rod driving mechanism 133, pass through the control rod cluster guide tubes 132, are extended to the fuel assemblies 120, and can hold the control rod cluster 131.

The control rod driving mechanism 133 is extended and provided in an up and down direction, and is connected with the control rod cluster 131. The control rod driving mechanism 133 controls an output of the nuclear reactor by moving the control rod cluster drive shafts 135 up and down with the magnetic jack, the control rod cluster drive shafts 135 having a plurality of peripheral grooves arranged and provided in the surfaces in a longitudinal direction with equal pitches.

Further, the reactor vessel main body 101*a* is provided with a large number of instrumentation nozzles 136 that penetrates the lower mirror 101*e*. An in-core side upper end portion of each of the instrumentation nozzles 136 is connected with an in-core instrumentation guide tube 137, and an ex-core side lower end portion is connected with a conduit tube 138. Upper end portions of the in-core instrumentation guide tubes 137 are connected with the lower core support 124, and upper and lower connection plates 139 and 140 for suppressing vibration are attached to the in-core instrumentation guide tubes 137. Thimble tubes 141 on which neutron flux detector (not illustrated) that can measure a neutron flux is mounted pass through the instrumentation nozzles 136 and the in-core instrumentation guide tubes 137 from the conduit tubes 138, penetrate the lower core support plate 128, and can be inserted to the fuel assemblies 120.

Therefore, the control rod cluster drive shafts 135 are moved by the control rod driving mechanism 133 and the control rods 130 are pulled out of the fuel assemblies 120 by a predetermined amount, so that nuclear fission in the reactor internal 129 is controlled. The light water filled in the reactor vessel 101 is heated by generated thermal energy, and the high-temperature light water is discharged through the output-side nozzle 101*d* and is sent to the steam generator 103, as described above. That is, the nuclear fuel that configures the fuel assemblies 120 performs the nuclear fission to release neutrons, and the light water as the moderator and the primary cooling water decreases kinetic energy of the released high-pressure neutrons, causes the neutrons to become thermal neutrons, facilitates new nuclear fission, and takes generated heat to perform cooling. Meanwhile, the number of neutrons generated in the reactor internal 129 is adjusted by insertion of the control rods 130 to the fuel assemblies 120. Further, the reactor can be urgently stopped by full insertion of the control rods 130 to the fuel assemblies 120.

Further, an upper plenum 142 communicating into the outlet-side nozzle 101*d* is formed above the reactor internal 129, and a lower plenum 143 is formed below the reactor internal 129, in the reactor vessel 101. Then, a downcomer portion 144 communicating into the inlet-side nozzle 101*c* and the lower plenum 143 is formed between the reactor vessel 101 and the core barrel 127. Therefore, the light water flows through the inlet-side nozzle 101*c* into the reactor vessel main body 101*a*, flows down in the downcomer portion 144 to reach the lower plenum 143, is upwardly guided along a spherical inner surface of the lower plenum 143 and rises, passes through the lower core support 124 and the lower core support plate 128, and then flows into the reactor internal 129. The light water having flown into the reactor internal 129 absorbs the thermal energy generated from the fuel assemblies 120 that configure the reactor internal 129 to cool the fuel assemblies 120, becomes to have a high temperature, passes through the upper core plate 126, rises to the upper plenum 142, and is discharged through the outlet-side nozzle 101*d*.

In the reactor vessel 101 configured as described above, as illustrated in FIG. 3, the instrumentation nozzle 136 is configured such that an in-core instrumentation cylinder 145 is fit into a mounting hole 146 formed in the lower mirror 101*e* of the reactor vessel main body 101*a*, and is fixed to an inner surface of the lower mirror 101*e* by welding (groove welded portion 147). The reactor vessel main body 101*a* is configured such that stainless steel is subjected to buttered welding on an inner surface of low alloy steel serving as a base material. The in-core instrumentation cylinder 145 made of a nickel-base alloy is welded (groove welded portion 147) to the reactor vessel main body 101*a* with a nickel-base alloy material in a state where the in-core instrumentation cylinder 145 is fit into the mounting hole 146 of the reactor vessel main body 101*a*.

Therefore, tensile stress may remain in the instrumentation nozzle 136 (in-core instrumentation cylinder 145), the groove welded portion 147, and its peripheral portions, and a probability of occurrence of stress corrosion cracking becomes high due to long-term use. Therefore, the tensile residual stress on a surface of the instrumentation nozzle 136 (in-core instrumentation cylinder 145), and a surface (inner surface) of the lower mirror 101*e* that is the groove welded portion 147 and its peripheral portion is improved into the compressive residual stress by a water jet peening device as a reactor repair device, so that the stress corrosion cracking is prevented. The water jet peening device is to jet high-pressure water containing cavitation bubbles on a surface of a metal member in water to improve the tensile residual stress on the surface of the metal member into the compressive residual stress.

When the tensile residual stress on the surface of the in-core instrumentation cylinder 145 and the surface of the lower mirror 101*e* is improved into the compressive residual stress by the water jet peening device, the water jet peening device is mounted to the instrumentation nozzle 136 (in-core instrumentation cylinder 145) and work is performed.

Figure 4:
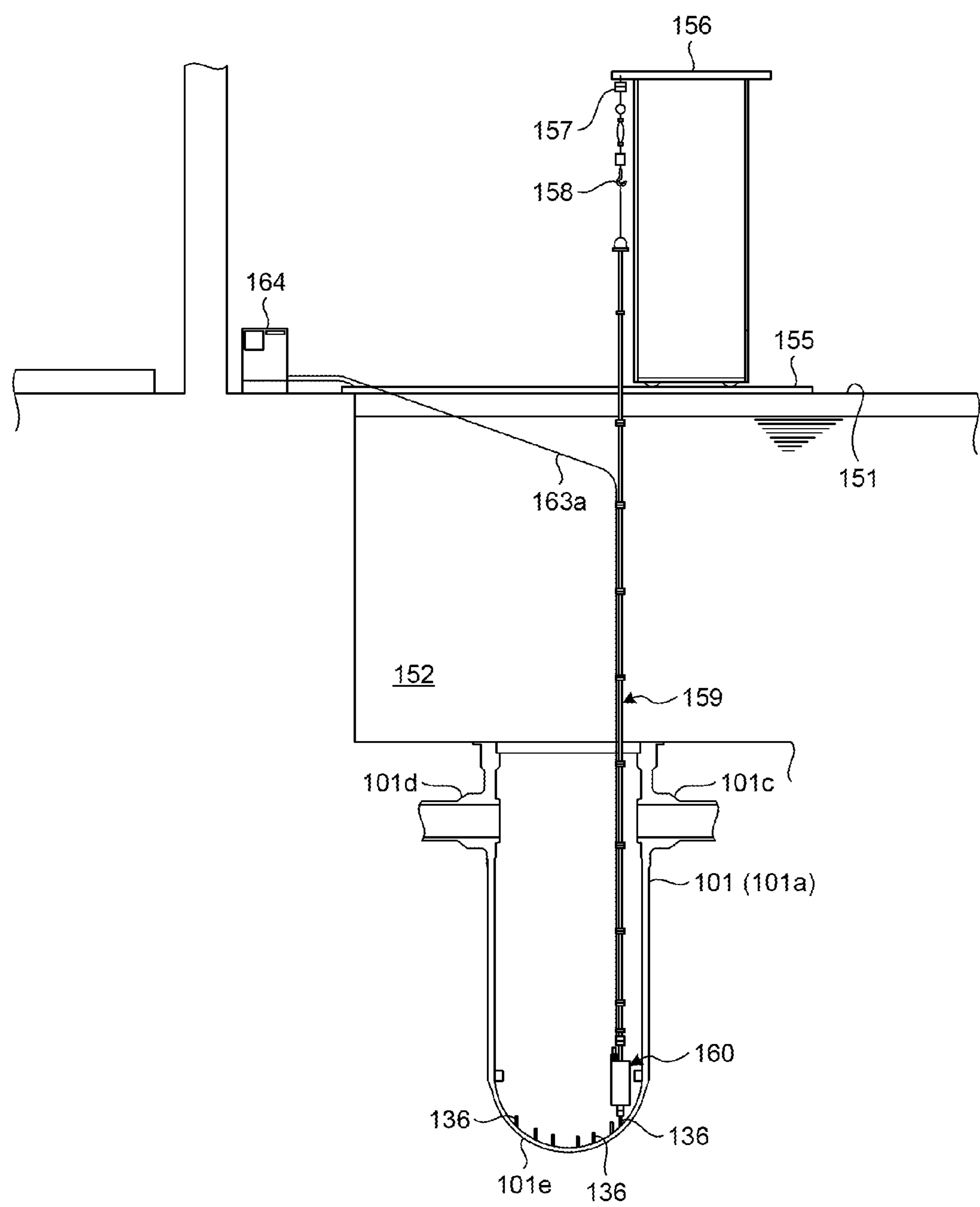
FIG. 4 is a schematic diagram illustrating an installation state of a water jet peening device.
Figure 5:
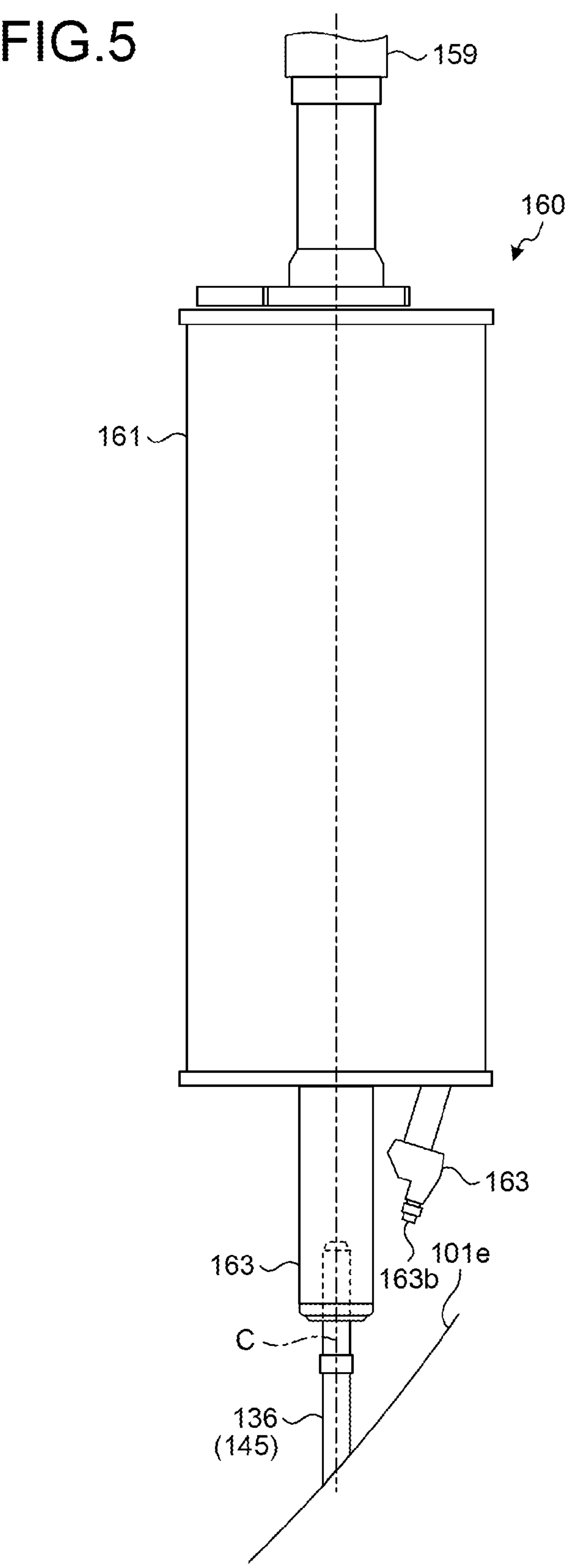
FIG. 5 is a front view of the water jet peening device.

FIG. 4 is a schematic diagram illustrating an installation state of a water jet peening device, and FIG. 5 is a front view of the water jet peening device.

As illustrated in FIG. 4, a water jet peening device 160 is installed to the instrumentation nozzle 136 (in-core instrumentation cylinder 145) provided on the lower mirror 101*e* of the reactor vessel 101 (reactor vessel main body 101*a*).

In the atomic power plant, a reactor building (not illustrated) is provided with a work floor 151. A cavity 152 is provided below the work floor 151, and the cooling water is stored in the cavity 152. The reactor vessel 101 is arranged inside the cavity 152, and is suspended and supported. In the reactor building, a pair of guide rails 155 is laid and provided on both sides of the cavity 152, and a mobile crane 156 is supported in a freely movable manner. The mobile crane 156 is provided with an electric hoist 157 freely movable in one direction in the horizontal direction (the right and left direction in FIG. 4), and freely movable in another direction intersecting with (perpendicular to) the one direction in the horizontal direction (the direction perpendicular to the paper surface in FIG. 4). Then, the electric hoist 157 includes a hook 158 that can be lifted along a vertical direction. An installation pole 159 is suspended through the hook 158.

The installation pole 159 is a long member and has a predetermine length, and the water jet peening device 160 can be connected to a lower end portion of the installation pole 159. The installation pole 159 is configured from a plurality of divided poles, and flange portions of upper and lower ends of the divided poles are caused to adhere to each other and fastened with a plurality of swing bolts.

As illustrated in FIG. 5, the water jet peening device 160 includes a device main body 161, a positioning member 162, and a jet nozzle 163. The positioning member 162 is arranged to protrude downward from a lower portion of the device main body 161, and fixes the device main body 161 to the instrumentation nozzle 136 by being fit into and clamping an upper portion of the instrumentation nozzle 136 (in-core instrumentation cylinder 145).

The jet nozzle 163 is provided to the device main body 161, and jets high-pressure water to an outer surface of the instrumentation nozzle 136 (in-core instrumentation cylinder 145), an inner surface of the lower mirror 101*e*, and the groove welded portion 147. A high-pressure water supply pipe 163*a* to which the high-pressure water is supplied is connected to the jet nozzle 163, as illustrated in FIG. 4. The high-pressure water supply pipe 163*a* is connected to the high-pressure water pump 164 installed on the work floor 151 and which sends the high-pressure water, as illustrated in FIG. 4. Further, the jet nozzle 163 is provided with a jet port 163*b* for jetting the water jet, at a lower end portion. The jet nozzle 163 is provided to swing around a central axis C of the instrumentation nozzle 136 (in-core instrumentation cylinder 145) and to lift along the central axis C, in a state where the positioning member 162 is fit into the upper end of the instrumentation nozzle 136 (in-core instrumentation cylinder 145) and clamped.

The water jet peening device 160 is suspended by the mobile crane 156 through the installation pole 159, in a state where the cooling water is stored in the cavity 152, as illustrated in FIG. 4. From there, the water jet peening device 160 is moved in a horizontal direction using the mobile crane 156, and is lowered using the electric hoist 157 while being positioned with respect to the instrumentation nozzle 136. Then, as illustrated in FIG. 5, the positioning member 162 is positioned to the upper end of the instrumentation nozzle 136, so that the water jet peening device 160 is fixed to the instrumentation nozzle 136.

When the water jet peening device 160 is fixed to the instrumentation nozzle 136, the jet nozzle 163 swings or is lifted while the high-pressure water is jetted through the jet port 163*b* of the jet nozzle 163, so that the high-pressure water including cavitation bubbles is jetted to the outer surface of the instrumentation nozzle 136 (in-core instrumentation cylinder 145), or the inner surface of the lower mirror 101*e*. Therefore, the tensile residual stress in the outer surface of the instrumentation nozzle 136 (in-core instrumentation cylinder 145) and the inner surface of the lower mirror 101*e* is improved into the compressive residual stress.

Note that, in the present embodiment, the installation pole 159 has been used as an installation tool used for installation of the water jet peening device 160. However, the installation tool is not limited to the configuration, and for example, a wire, a cable, a rope, or the like may be used.

Figure 6:
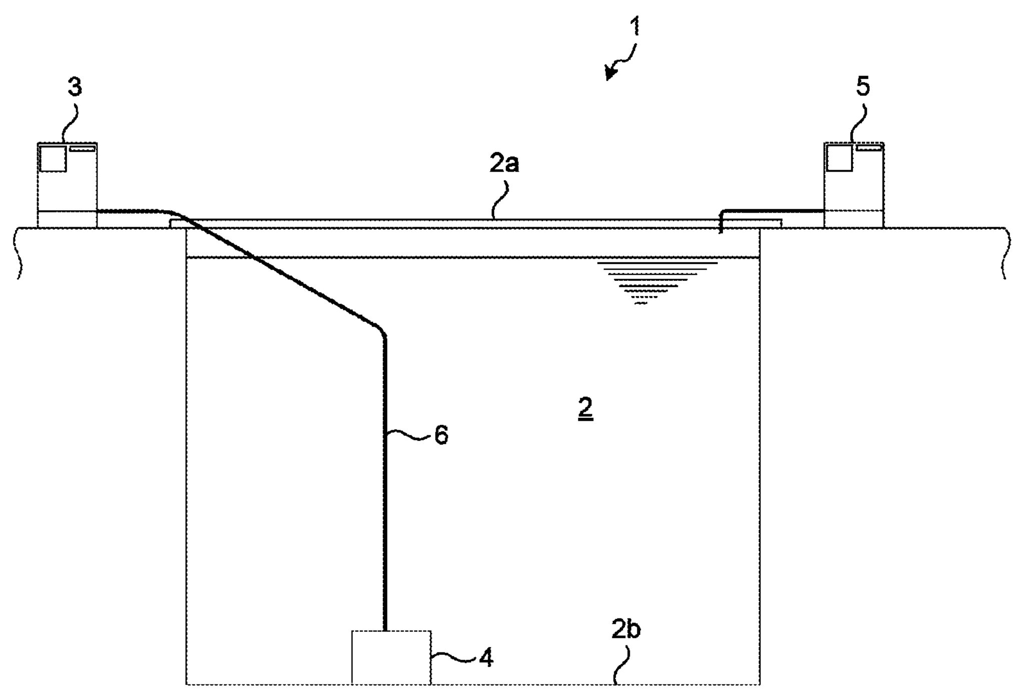
FIG. 6 is a schematic diagram of a water jet peening compressive residual stress test facility according to an embodiment of the present invention.

By the way, in the present embodiment, a water jet peening compressive residual stress facility for confirming the degree and the size of a result of providing the compressive residual stress is provided in the above-described water jet peening. FIG. 6 is a schematic diagram of a water jet peening compressive residual stress test facility according to the present embodiment.

As illustrated in FIG. 6, a water jet peening compressive residual stress test facility 1 is used to perform a water jet peening compressive residual stress test, and includes a water tank 2, a high-pressure water pump 3, and a water jet peening compressive residual stress test device 4.

The water tank 2 forms an underwater environment. The underwater environment includes the reactor vessel 101 in which the water jet peening is carried out, and an underwater environment that simulates an environment in which the water jet peening is carried out, and can store water therein. The water tank 2 may have a depth similar to the reactor vessel 101 in order to form the underwater environment. Further, the water tank 2 may simulate the depth similar to the reactor vessel 101 by being sealed with a water tank cover (sealing means) 2*a* that covers an opening of an upper portion, and being pressurized by pressurizing means 5. The high-pressure water pump 3 is similar to the above-described high-pressure water pump 164, and is connected with a high-pressure water supply pipe 6. Further, although details will be described below, the water jet peening compressive residual stress test device 4 holds a plastically deformable almen strip, and to which the jet port 163*b* of the jet nozzle 163 in the water jet peening device 160 is mounted and the high-pressure water supply pipe 6 is connected.

In the water jet peening compressive residual stress test facility 1, the high-pressure water supply pipe 6 is connected to the water jet peening compressive residual stress test device 4 and the high-pressure water pump 3, and the high-pressure water is supplied to the water jet peening compressive residual stress test device 4 through the high-pressure water supply pipe 6, so that the water jet is jetted to the almen strip through the jet port 163*b*. Then, plastic deformation of the almen strip is measured, so that the degree and the size of a result of providing compressive residual stress provided in the water jet peening can be confirmed.

As described above, the water jet peening compressive residual stress test facility 1 of the present embodiment includes the water tank 2 that forms a predetermined underwater environment, and the high-pressure water pump 3 that sends the high-pressure water to the high-pressure water supply pipe 6 that supplies the high-pressure water, arranges the water jet peening compressive residual stress test device 4 in the underwater environment of the water tank 2, connects the high-pressure water supply pipe 6 to the water jet peening compressive residual stress test device 4 and the high-pressure water pump 3, and performs the water jet peening compressive residual stress test.

According to the water jet peening compressive residual stress test facility 1, the degree and the size of a result of providing compressive residual stress in the water jet peening can be confirmed.

Note that the jet port 163*b* and the high-pressure water supply pipe 6 are mounted the water jet peening compressive residual stress test device 4 before the water jet peening is actually carried out by the water jet peening device 160, and after replaced after the water jet peening is carried out, and the water jet peening compressive residual stress test is performed. In doing so, the degree and the size of a result of providing compressive residual stress in the water jet peening carried out with the jet port 163*b* and the high-pressure water supply pipe 6 actually used for execution of the water jet peening can be confirmed.

Further, the water jet peening compressive residual stress test facility 1 of the present embodiment includes the water tank cover 2*a* that seals the inside of the water tank 2, and the pressurizing means 5 that pressurizes the inside of the sealed water tank 2.

According to the water jet peening compressive residual stress test facility 1, an actual underwater environment in which the water jet peening is carried out can be simulated, and confirmation accuracy of the degree and the size of a result of providing compressive residual stress in the water jet peening can be improved.

Further, a water jet peening compressive residual stress test method of the present embodiment holds a plastically deformable almen strip under a predetermined underwater environment in which water jet peening is carried out, and jets water jet to the almen strip.

According to the water jet peening compressive residual stress test method, the degree and the size of a result of providing compressive residual stress in the water jet peening can be confirmed.

Further, the water jet peening compressive residual stress test method of the present embodiment provides the underwater environment by putting water in the sealed water tank 2 and pressurizes the sealed water tank 2, holds the almen strip under the underwater environment, and jets the water jet to the almen strip.

According to the water jet peening compressive residual stress test method, an actual underwater environment in which the water jet peening is carried out can be simulated, and confirmation accuracy of the degree and the size of a result of providing compressive residual stress in the water jet peening can be improved.

Figure 7:
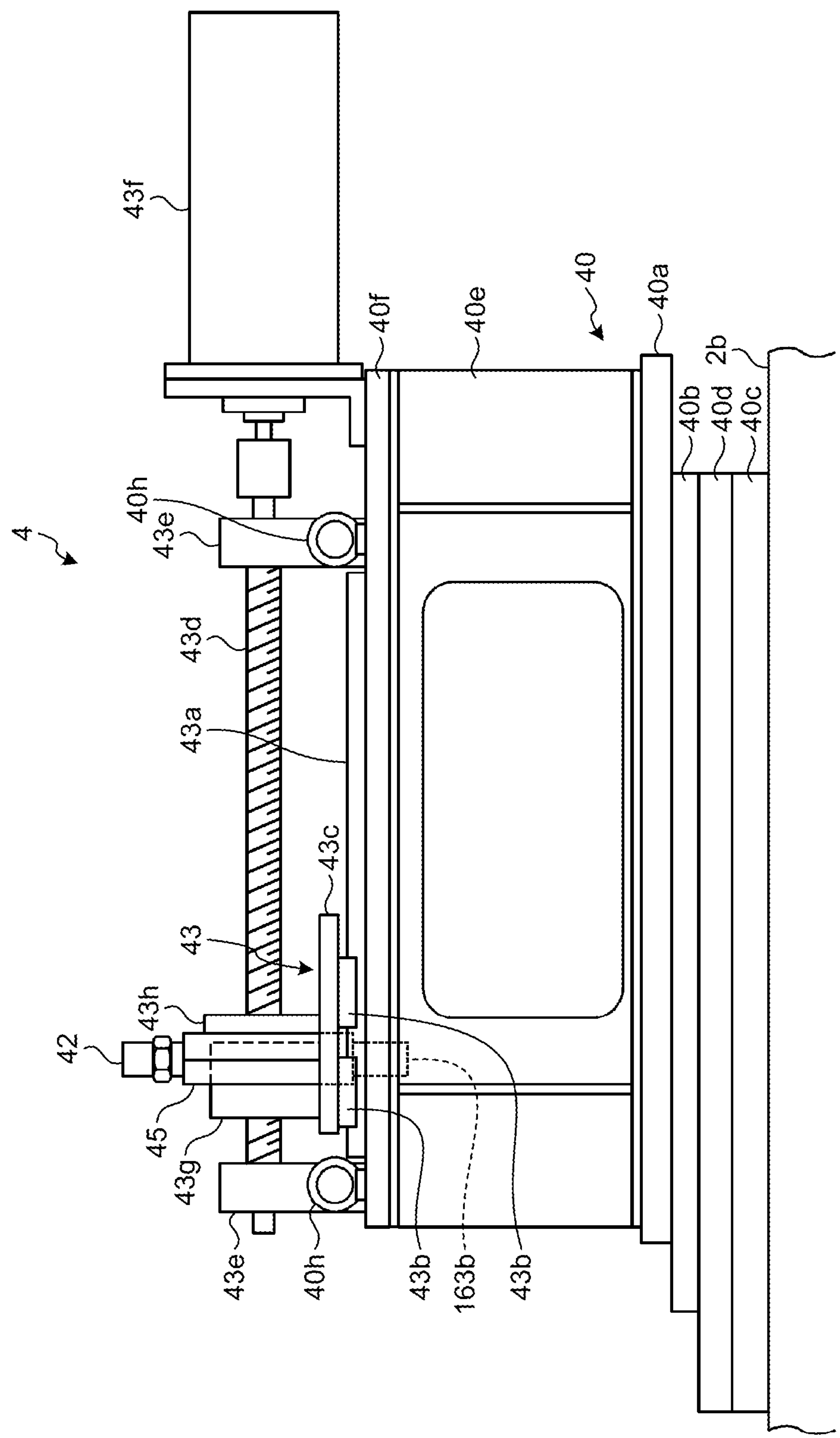
FIG. 7 is a side view of a water jet peening compressive residual stress test device according to an embodiment of the present invention.
Figure 8:
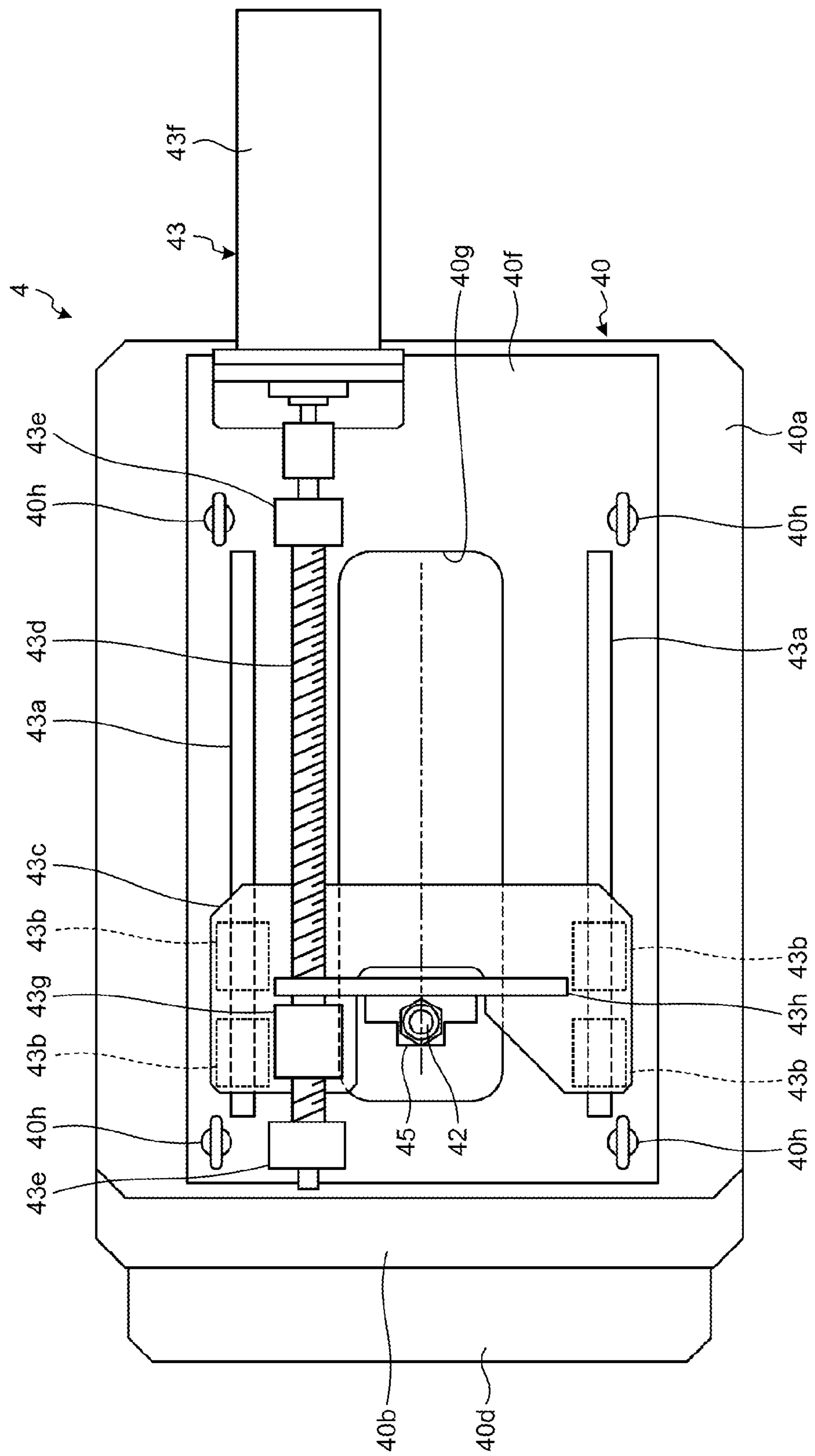
FIG. 8 is a plan view of a water jet peening compressive residual stress test device according to an embodiment of the present invention.
Figure 9:
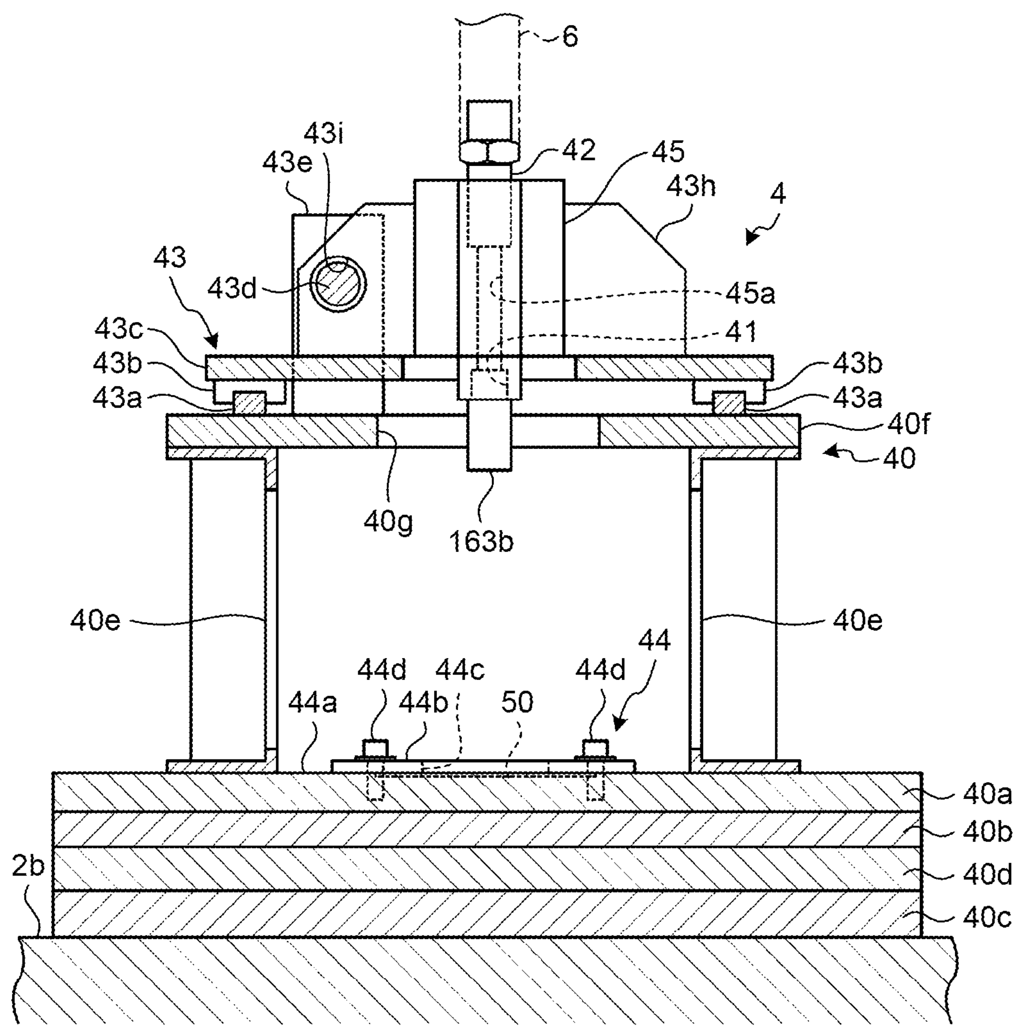
FIG. 9 is a longitudinal sectional view of a water jet peening compressive residual stress test device according to an embodiment of the present invention.
Figure 10:
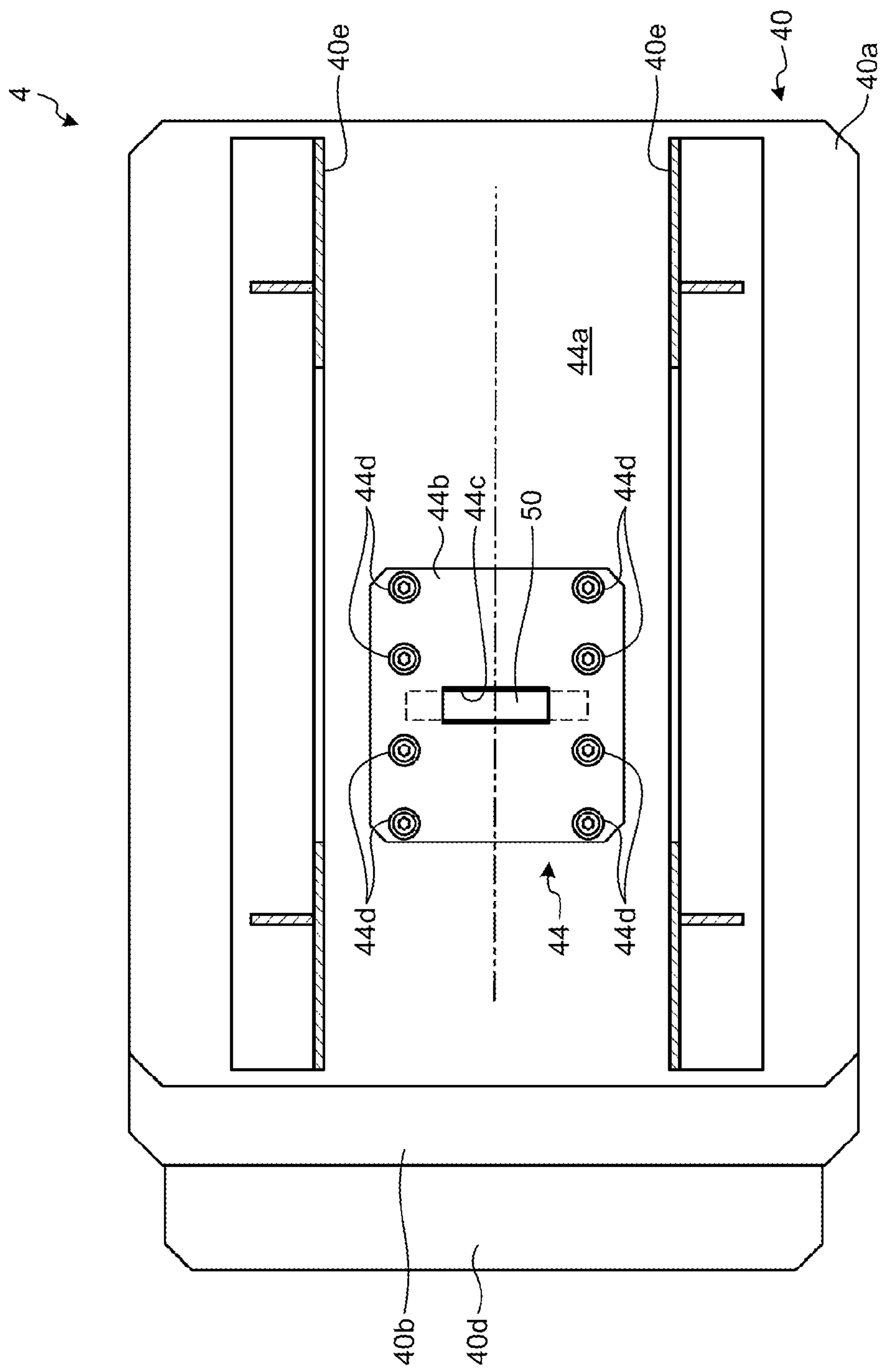
FIG. 10 is a transverse sectional view of a water jet peening compressive residual stress test device according to an embodiment of the present invention.

Hereinafter, the water jet peening compressive residual stress test device 4 will be described. FIG. 7 is a side view of a water jet peening compressive residual stress test device according to the present embodiment. FIG. 8 is a plan view of a water jet peening compressive residual stress test device according to the present embodiment. FIG. 9 is a longitudinal sectional view of a water jet peening compressive residual stress test device according to the present embodiment. FIG. 10 is a transverse sectional view of a water jet peening compressive residual stress test device according to the present embodiment.

As illustrated in FIGS. 7 to 10, the water jet peening compressive residual stress test device 4 of the present embodiment includes a device main body 40, a jet port mounting portion 41, a high-pressure water pipe mounting portion 42, a slide-moving mechanism 43, and an almen strip holding portion 44.

The device main body 40 includes a flat support plate 40*a*. The support plate 40*a* is arranged on a bottom surface 2*b* of the water tank 2. Therefore, a substrate 40*b* and a bottom plate 40*c* are fixed to the bottom surface. A spacer 40*d* is arranged between the substrate 40*b* and the bottom plate 40*c*, as needed. Further, side plates 40*e* are fixed to an upper surface of the support plate 40*a* of the device main body 40. The side plates 40*e* are installed on both side portions of the support plate 40*a* in a standing manner, and arranged to face each other, as illustrated in FIGS. 9 and 10. A top plate 40*f* is disposed across upper ends of the side plates 40*e* in parallel to the support plate 40*a*. A through hole 40*g* facing the support plate 40*a* from above is formed in a central portion of the top plate 40*f*, as illustrated in FIGS. 8 and 9. Further, locking members 40*h*, with which suspension wires or the like are locked at the time of suspension of the water jet peening compressive residual stress test device 4, are provided at four corners on an upper surface of the top plate 40*f*.

The jet port mounting portion 41 includes a female screw hole into which the jet port 163*b* is mounted, as illustrated in FIG. 9, the jet port 163*b* jetting the water jet in the jet nozzle 163. The jet port 163*b* mounted to the jet port mounting portion 41 faces the upper surface of the support plate 40*a* through the through hole 40*g*.

The high-pressure water pipe mounting portion 42 includes a connection pipe to which an end portion of the high-pressure water supply pipe 6 is connected, as illustrated in FIG. 9, the high-pressure water supply pipe 6 being connected with the high-pressure water pump 3 in the water jet peening compressive residual stress test facility 1.

The jet port mounting portion 41 and the high-pressure water pipe mounting portion 42 are provided in a mounting base 45, as illustrated in FIG. 9. The mounting base 45 is provided with a through hole 45*a*, into which the female screw of the jet port mounting portion 41 and the connection pipe of the high-pressure water pipe mounting portion 42 communicate. That is, the jet port 163*b* mounted to the jet port mounting portion 41 and the high-pressure water supply pipe 6 mounted to the high-pressure water pipe mounting portion 42 communicate into each other through the through hole 45*a* of the mounting base 45, and the high-pressure water sent from the high-pressure water pump 3 through the high-pressure water supply pipe 6 is jetted through the jet port 163*b* as the water jet.

The slide-moving mechanism 43 slides and moves the mounting base 45 in which the jet port mounting portion 41 and the high-pressure water pipe mounting portion 42 are provided. The slide-moving mechanism 43 is provided on the top plate 40*f* of the device main body 40, as illustrated in FIGS. 7 and 8, and includes slide rails 43*a*, sliders 43*b*, a slide frame 43*c*, a ball screw 43*d*, rotation support portions 43*e*, a slide motor 43*f*, a moving member 43*g*, and an attaching member 43*h*. The slide rails 43*a* are fixed to the upper surface of the top plate 40*f*, and are provided extending in parallel on both side portions of the through hole 40*g*. An extending direction of the slide rails 43*a* is a direction perpendicular to the direction that the jet port 163*b* mounted to the jet port mounting portion 41 faces. The sliders 43*b* are supported in a movable manner in the extending direction of the slide rails 43*a*. The slide frame 43*c* is supported by the sliders 43*b*, and is provided in a movable manner in the extending direction of the slide rails 43*a*. The ball screw 43*d* is provided in parallel to the slide rails 43*a*, and both ends of the ball screw 43*d* are rotatably supported by the pair of rotation support portions 43*e* fixed to the upper surface of the top plate 40*f*. The slide motor 43*f* is fixed to the upper surface of the top plate 40*f*, and an output shaft of the slide motor 43*f* is connected with one end of the ball screw 43*d*. The moving member 43*g* is made of a nut screwed into the ball screw 43*d*, and is fixed to the slide frame 43*c*. The attaching member 43*h* is fixed to the slide frame 43*c*, and the mounting base 45 provided with the jet port mounting portion 41 and the high-pressure water pipe mounting portion 42 is attached to the attaching member 43*h*. Further, the attaching member 43*h* includes an insertion hole 43*i* into which the ball screw 43*d* is inserted without allowing the ball screw 43*d* to be in contact with the insertion hole 43*i*. Then, in the slide-moving mechanism 43, the ball screw 43*d* is rotated by driving of the slide motor 43*f*, and the moving member 43*g* is slid and moved together with the slide frame 43*c* in the extending direction of the ball screw 43*d* (the extending direction of the slide rails 43*a*). That is, the mounting base 45 is slid and moved with the slide movement of the slide frame 43*c*. As a result, the jet port 163*b* mounted to the jet port mounting portion 41 and the high-pressure water supply pipe 6 mounted to the high-pressure water pipe mounting portion 42 in the mounting base 45 are slid and moved in the extending direction of the ball screw 43*d* (the extending direction of the slide rails 43*a*), and along a moving locus illustrated in FIG. 8 by the two-dot chain line and perpendicular to and the direction into which the jet port 163*b* mounted to the jet port mounting portion 41 faces.

The almen strip holding portion 44 is used to attach an almen strip 50 to the support plate 40*a*, and includes, as illustrated in FIGS. 9 and 10, a support surface 44*a* that is the upper surface of the support plate 40*a*, and attaching portions 44*b* and 44*d*. Here, the almen strip 50 is a plastically deformable test piece formed into a plate shape. The almen strip holding portion 44 allows a plate surface of the almen strip 50 to be in contact with and attached to the support surface 44*a* with the attaching portions 44*b* and 44*d*. Therefore, the plate surface of the almen strip 50 is held facing the jet port 163*b* mounted to the jet port mounting portion 41. Details of the almen strip holding portion 44 will be described below.

Such a water jet peening compressive residual stress test device 4 is arranged under the underwater environment of the water tank 2 in the water jet peening compressive residual stress test facility 1, as described above, in the embodiment in which the jet port 163*b* is mounted to the jet port mounting portion 41, the end portion of the high-pressure water supply pipe 6 connected to the high-pressure water pump 3 is mounted to the high-pressure water pipe mounting portion 42, and the almen strip 50 is held in the almen strip holding portion 44. Then, the water jet is jetted through the jet port 163*b* to the almen strip 50 under the underwater environment, so that the water jet peening is applied, and the almen strip 50 is plastically deformed. Then, the plastic deformation of the almen strip 50 is measured, so that the degree and the size of a result of providing compressive residual stress provided in the water jet peening can be confirmed.

Figure 11:
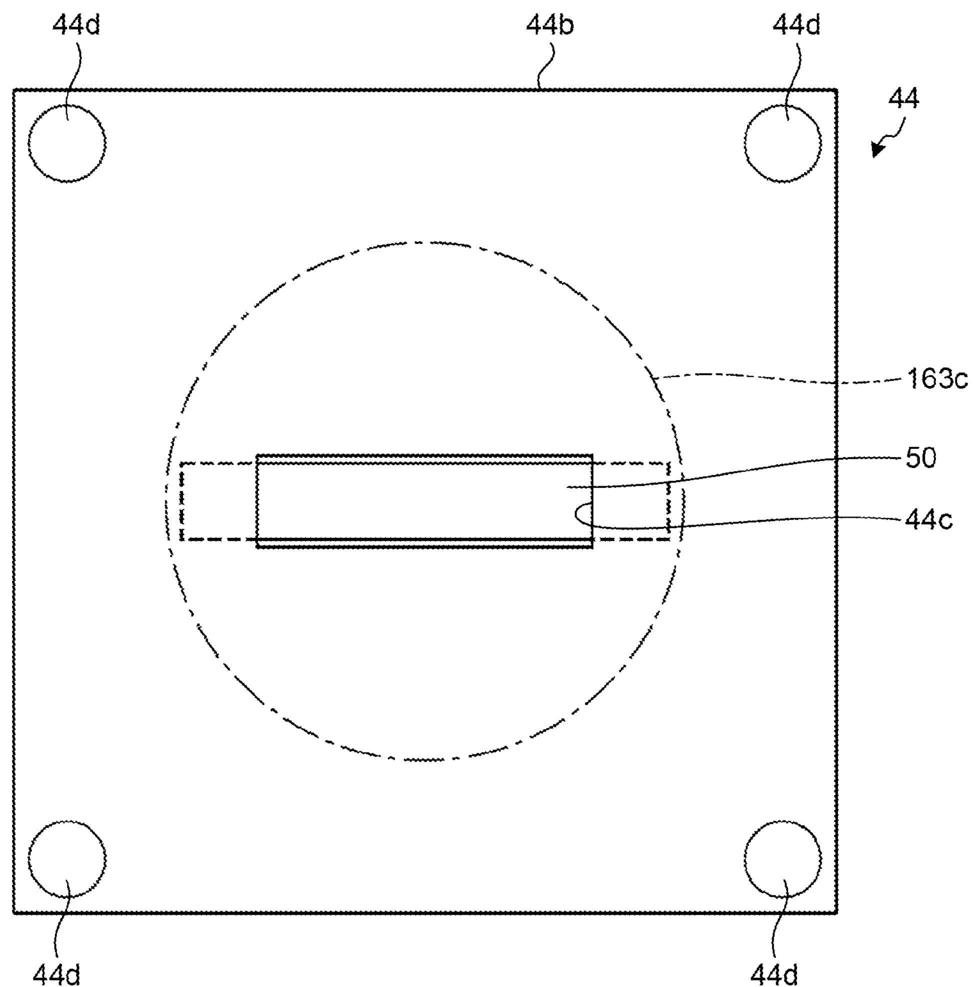
FIG. 11 is a plan view illustrating an almen strip holding portion of a water jet peening compressive residual stress test device according to an embodiment of the present invention.
Figure 12:
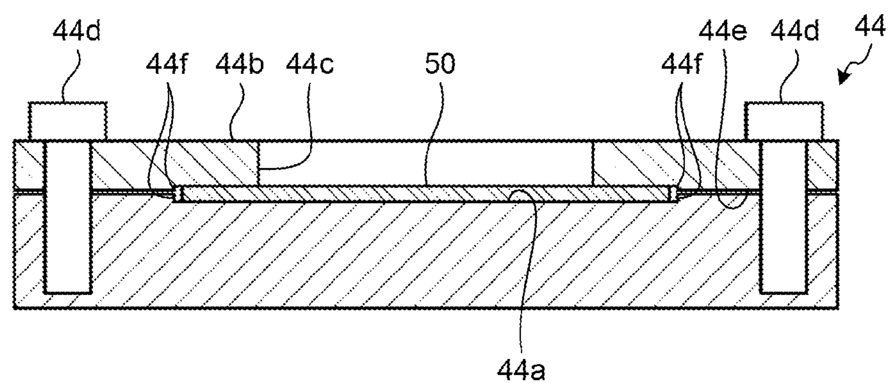
FIG. 12 is a longitudinal sectional view in FIG. 11.
Figure 13:
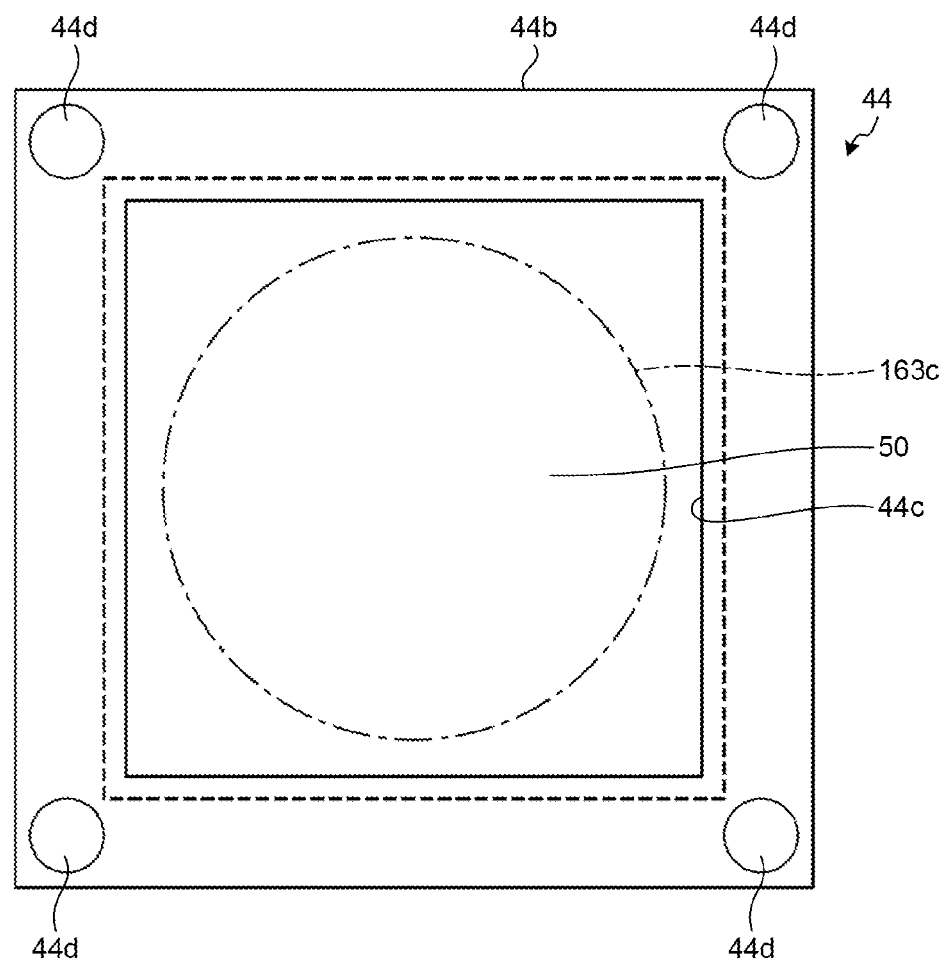
FIG. 13 is a plan view illustrating another example of an almen strip holding portion of a water jet peening compressive residual stress test device according to an embodiment of the present invention.
Figure 14:
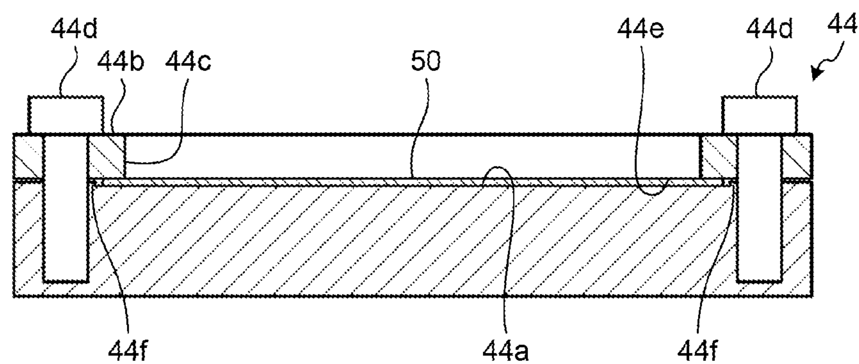
FIG. 14 is a longitudinal sectional view in FIG. 13.
Figure 15:
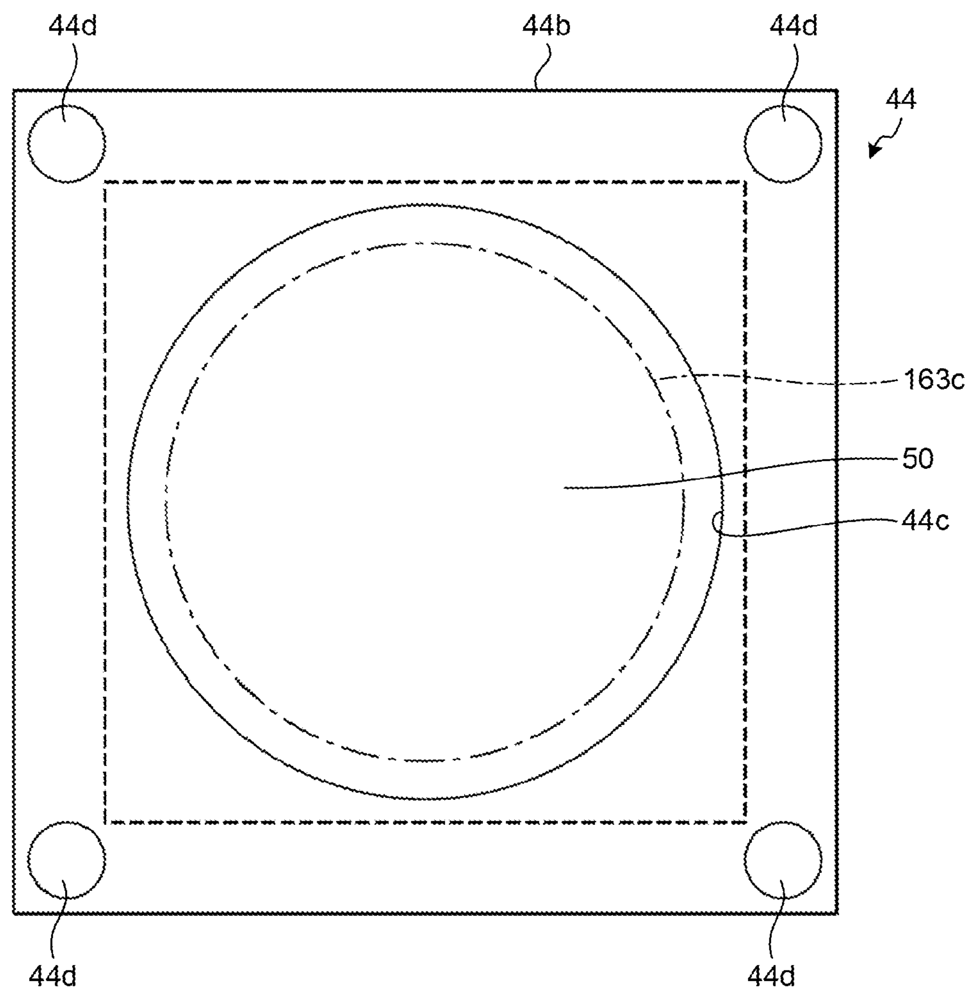
FIG. 15 is a plan view illustrating another example of an almen strip holding portion of a water jet peening compressive residual stress test device according to an embodiment of the present invention.
Figure 16:
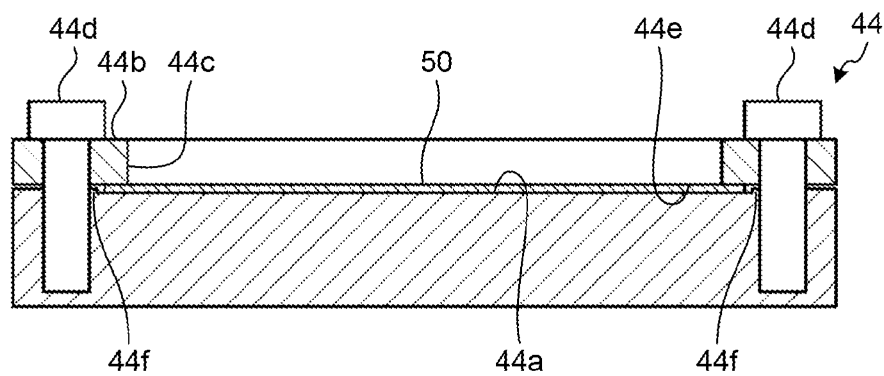
FIG. 16 is a longitudinal sectional view in FIG. 15.
Figure 17:
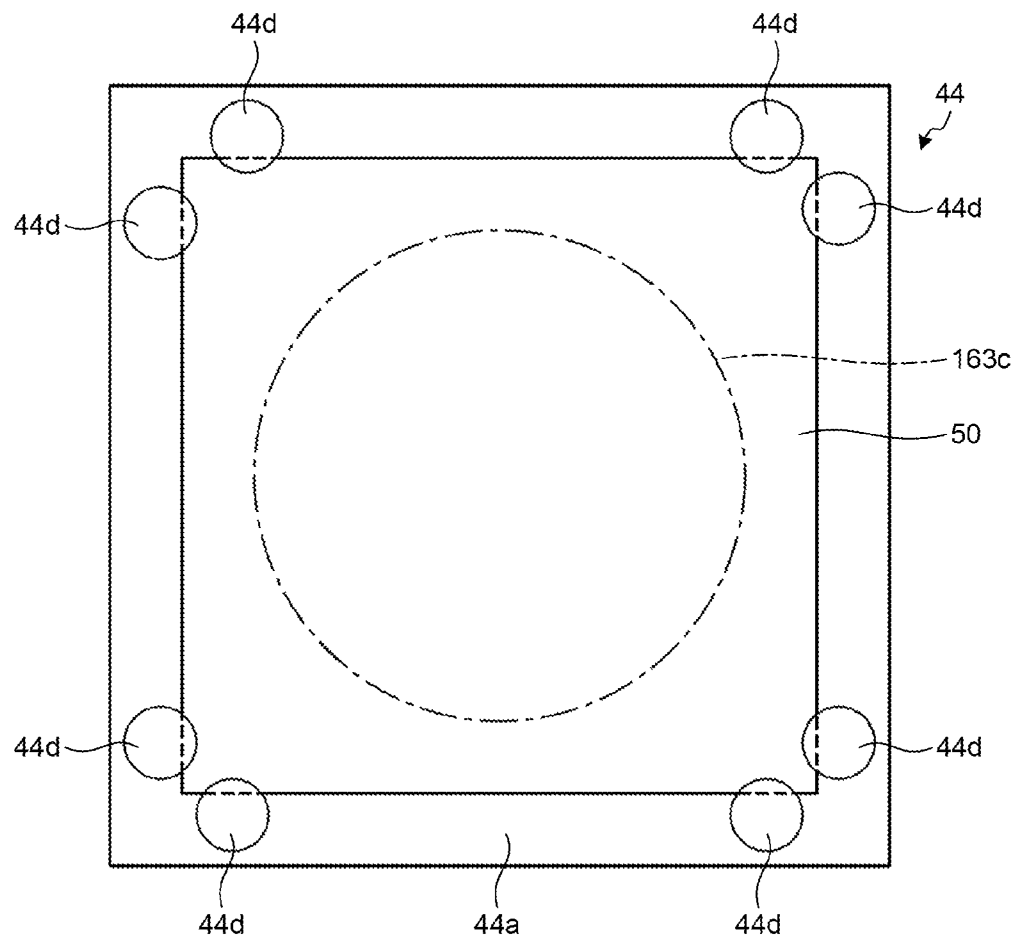
FIG. 17 is a plan view illustrating another example of an almen strip holding portion of a water jet peening compressive residual stress test device according to an embodiment of the present invention.
Figure 18:
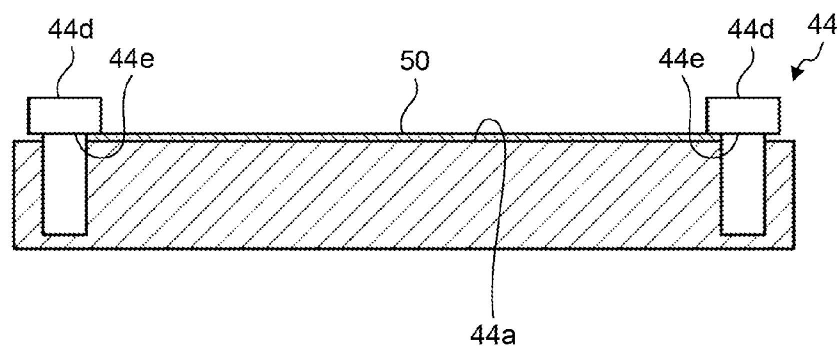
FIG. 18 is a longitudinal sectional view in FIG. 17.
Figure 19:
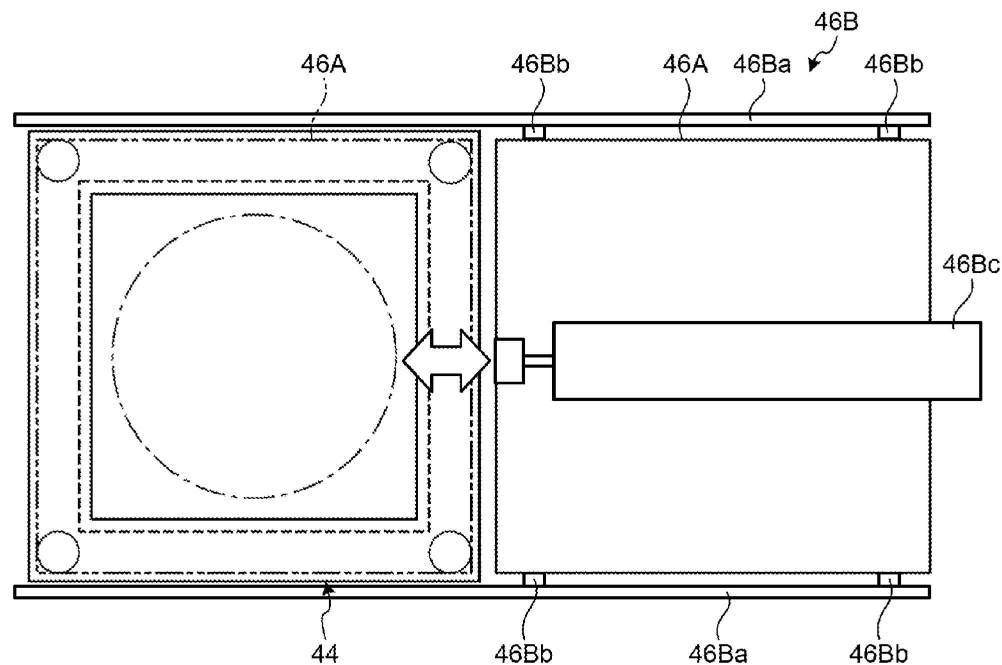
FIG. 19 is a plan view illustrating another example of an almen strip holding portion of a water jet peening compressive residual stress test device according to an embodiment of the present invention.
Figure 20:
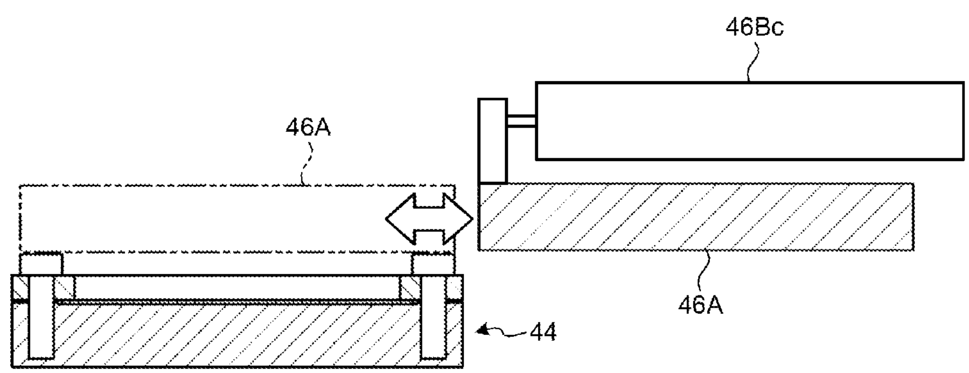
FIG. 20 is a longitudinal sectional view in FIG. 19.
Figure 21:
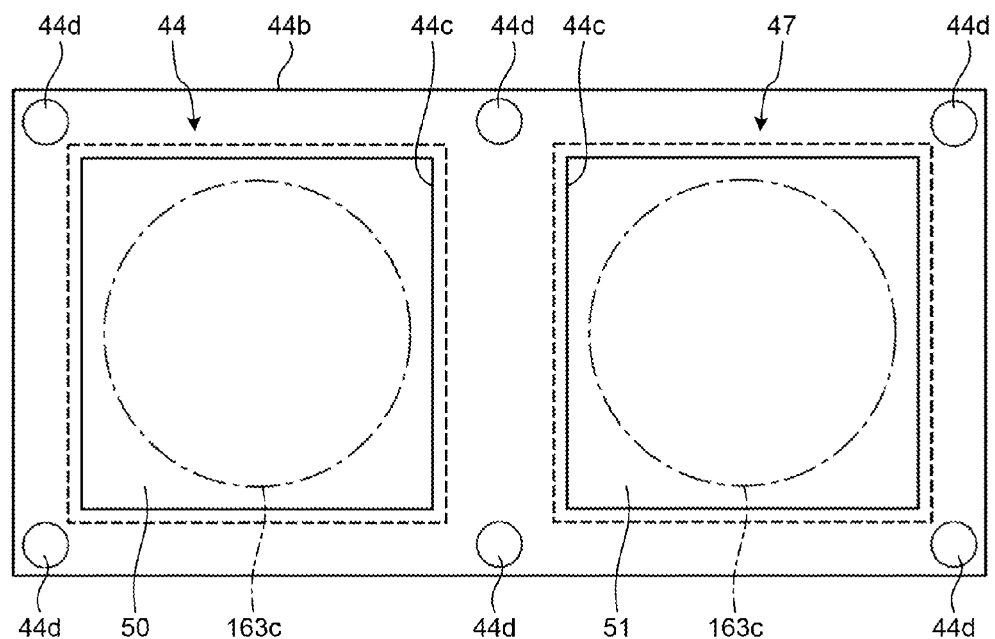
FIG. 21 is a plan view illustrating another example of an almen strip holding portion of a water jet peening compressive residual stress test device according to an embodiment of the present invention.
Figure 22:
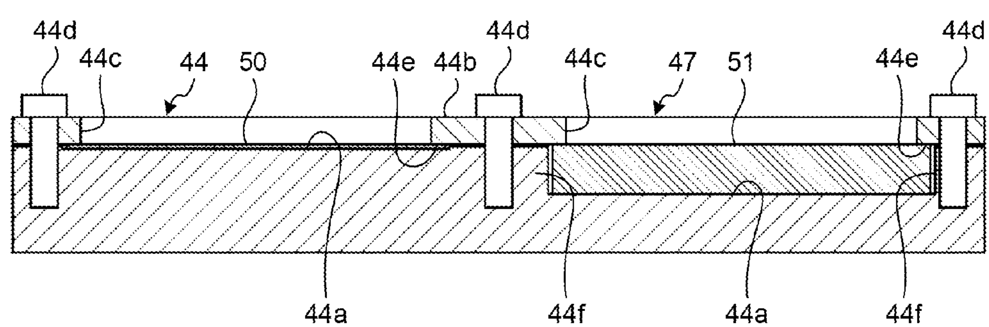
FIG. 22 is a longitudinal sectional view in FIG. 21.

Hereinafter, the almen strip holding portion 44 will be described. FIG. 11 is a plan view illustrating an almen strip holding portion of a water jet peening compressive residual stress test device according to the present embodiment. FIG. 12 is a longitudinal sectional view in FIG. 11. FIG. 13 is a plan view illustrating another example of an almen strip holding portion of a water jet peening compressive residual stress test device according to the present embodiment. FIG. 14 is a longitudinal sectional view in FIG. 13. FIG. 15 is a plan view illustrating another example of an almen strip holding portion of a water jet peening compressive residual stress test device according to the present embodiment. FIG. 16 is a longitudinal sectional view in FIG. 15. FIG. 17 is a plan view illustrating another example of an almen strip holding portion of a water jet peening compressive residual stress test device according to the present embodiment. FIG. 18 is a longitudinal sectional view in FIG. 17. FIG. 19 is a plan view illustrating another example of an almen strip holding portion of a water jet peening compressive residual stress test device according to the present embodiment. FIG. 20 is a longitudinal sectional view in FIG. 19. FIG. 21 is a plan view illustrating another example of an almen strip holding portion of a water jet peening compressive residual stress test device according to the present embodiment. FIG. 22 is a longitudinal sectional view in FIG. 21.

An almen strip holding portion 44 illustrated in FIGS. 11 and 12 is similar to the almen strip holding portion 44 illustrated in FIGS. 9 and 10. The almen strip holding portion 44 allows, as described above, the plate surface of the almen strip 50 to be in contact with and attached to the support surface 44*a*, and includes a pressing member 44*b* and fixing members 44*d* as the attaching portions. The pressing member 44*b* is provided with a through hole 44*c* that allows the plate surface of the almen strip 50, to which the water jet is jetted, to let out, and includes a pressing surface 44*e* abutting on an outer edge of the almen strip 50. The fixing members 44*d* are configured as bolts, and fix at least four corners (eight corners in FIG. 10) of the pressing member 44*b* formed into a rectangular plate shape to the support surface 44*a* (the upper surface of the support plate 40*a* in the water jet peening compressive residual stress test device 4). The almen strip 50 illustrated in FIGS. 11 and 12 is a strip-shaped plate material formed to have a plate thickness of 1 to 2 mm. The through hole 44*c* is formed to be smaller than the dimension of the almen strip 50 in the longitudinal direction, and to be slightly larger than the dimension of the almen strip 50 in the short direction, so that the pressing member 44*b* presses both end portions of the almen strip 50 in the longitudinal direction with the pressing surface 44*e*.

The almen strip holding portion 44 illustrated in FIGS. 11 and 12 is arranged such that the through hole 44*c* of the pressing member 44*b* is positioned directly under the jet port mounting portion 41 in the water jet peening compressive residual stress test device 4. Further, the almen strip holding portion 44 illustrated in FIGS. 11 and 12 has the through hole 44*c* formed to fall within an effective range 163*c* where the water jet peening acts. The effective range 163*c* where the water jet peening acts varies according to the depth of water (water pressure). However, in the present embodiment, the effective range 163*c* is a diameter of 50 mm, as an example. The water jet is jetted through the jet port 163*b* mounted to the jet port mounting portion 41 to a portion of the almen strip 50 let out through the through hole 44*c*, so that the water jet peening is applied to the portion. The almen strip 50 to which the water jet peening is applied is plastically deformed such that both end portion in the longitudinal direction get closer to each other. Therefore, the degree and the size of a result of providing compressive residual stress provided in the water jet peening can be confirmed by measurement of the plastic deformation of the almen strip 50.

As described above, in the almen strip holding portion 44 of the water jet peening compressive residual stress test device 4 of the present embodiment, the attaching portions include the pressing member 44*b* including the through hole 44*c* through which the portion of the almen strip 50, to which the water jet is jetted, is let out, and the pressing surface 44*e* abutting on the outer edge of the almen strip 50, and the fixing members 44*d* that fix the pressing member 44*b* to sandwich the almen strip 50 between the pressing surface 44*e* of the pressing member 44*b* and the support surface 44*a*. Therefore, the water jet peening is applied to the portion of the almen strip 50 let out through the through hole 44*c*. Then, when the water jet is jetted to the almen strip 50, the inflow of the water jet to a portion not let out through the through hole 44*c* due to the through hole 44*c*, and between the almen strip 50 and the support surface 44*a*. As a result, the plastic deformation of the almen strip 50 by an action other than the water jet peening is suppressed, and more highly accurate evaluation of the compressive residual stress provided in the water jet peening can be performed.

Further, as illustrated in FIGS. 11 and 12, the almen strip holding portion 44 includes a recessed portion 44*f* formed to surround a vicinity of the almen strip 50 in at least one of the support surface 44*a* and the pressing surface 44*e*. The recessed portion 44*f* is formed and provided such that the almen strip 50 is inserted to the support surface 44*a* or the pressing surface 44*e*. Further, the recessed portion 44*f* may be formed by providing a protrusion that surrounds the vicinity of the almen strip 50 in the support surface 44*a* or the pressing surface 44*e*. The almen strip holding portion 44 illustrated in FIGS. 11 and 12 is an embodiment in which the recessed portions 44*f* are provided in the support surface 44*a* and the pressing surface 44*e*.

As described above, the recessed portion 44*f* that allows the almen strip 50 to be inserted to surround the vicinity of the almen strip 50 is provided in at least one of the support surface 44*a* and the pressing surface 44*e*, so that the inflow of the water jet to between the almen strip 50 and the support surface 44*a* is further suppressed with a step of an outer periphery of the recessed portion 44*f* when the water jet is jetted to the almen strip 50. Therefore, deformation of the almen strip 50 due to the inflow of the water jet to between the almen strip 50 and the support surface 44*a* is further suppressed. As a result, the plastic deformation of the almen strip 50 by an action other than the water jet peening is suppressed, and more highly accurate evaluation of the compressive residual stress provided in the water jet peening can be performed.

The almen strip holding portion 44 illustrated in FIGS. 13 and 14 allows the plate surface of the almen strip 50 to be in contact with and attached to the support surface 44*a*, and includes the pressing member 44*b* and the fixing members 44*d* as the attaching portions, as described above. The support surface 44*a* of the almen strip holding portion 44 has an area broader than the effective range where the water jet acts. The pressing member 44*b* is provided with the rectangular through hole 44c that allows the plate surface to which the water jet of the almen strip 50 is jetted to be let out, and includes the pressing surface 44e abutting on the outer edge of the almen strip 50. The fixing members 44d are configured as bolts, and fix at least four corners of the pressing member 44b formed into a rectangular shape to the support surface 44a (the upper surface of the support plate 40a in the water jet peening compressive residual stress test device 4). The almen strip 50 illustrated in FIGS. 13 and 14 is a rectangular plate member formed to have the plate thickness of about 1 to 2 mm, and having an area broader than the effective range 163c where the water jet acts. In the pressing member 44b, the through hole 44c is formed to be opened broader than the effective range 163c where the water jet acts. Therefore, the pressing member 44b is configured to press the vicinity of the almen strip 50 with the pressing surface 44e, spacing an area broader than the effective range 163c.

The almen strip holding portion 44 illustrated in FIGS. 13 and 14 is arranged such that the through hole 44c of the pressing member 44b is positioned directly under the jet port mounting portion 41 in the water jet peening compressive residual stress test device 4. Then, the water jet is jetted through the jet port 163b mounted to the jet port mounting portion 41 to the portion of the effective range 163c of the almen strip 50 let out through the through hole 44c, so that the water jet peening is applied to the portion. The effective range 163c where the water jet acts, of the almen strip 50 subjected to the water jet peening, is plastically deformed. Therefore, the degree and the size of a result of providing compressive residual stress provided in the water jet peening can be confirmed by measurement of the plastic deformation of the almen strip 50 is measured.

As described above, in the almen strip holding portion 44 of the water jet peening compressive residual stress test device 4 of the present embodiment, the support surface 44a has an area broader than the effective range 163c where the water jet acts, the attaching portions (the pressing member 44b and the fixing members 44d) allow the almen strip 50 to be attached, spacing an area broader than the effective range 163c, the water jet peening is applied to the portion of the effective range 163c of the almen strip 50, the portion being let out through the through hole 44c. Therefore, when the water jet is jetted to the almen strip 50, the inflow of the water jet to the portion not let out through the through hole 44c, and the portion between the almen strip 50 and the support surface 44a is suppressed. As a result, the plastic deformation of the almen strip 50 by an action other than the water jet peening is suppressed, and more highly accurate evaluation of the compressive residual stress provided in the water jet peening can be performed.

An almen strip holding portion 44 illustrated in FIGS. 15 and 16 is obtained such that the through hole 44c of the almen strip holding portion 44 illustrated in FIGS. 13 and 14 is formed into a circle. With such a configuration, the water jet peening is applied to the portion of the effective range 163c of the almen strip 50 let out through the through hole 44c. Then, when the water jet is jetted to the almen strip 50, the inflow of the water jet to the portion not let out through the through hole 44c, and the portion between the almen strip 50 and the support surface 44a is suppressed. As a result, the plastic deformation of the almen strip 50 by an action other than the water jet peening is suppressed, and more highly accurate evaluation of the compressive residual stress provided in the water jet peening can be performed.

Further, in the almen strip holding portion 44 illustrated in FIGS. 13 to 16, the recessed portion 44f that allows the almen strip 50 to be inserted to surround the vicinity of the almen strip 50 is provided in at least one of the support surface 44a and the pressing surface 44e, so that the inflow of the water jet to between the almen strip 50 and the support surface 44a is further suppressed with the step of the outer periphery of the recessed portion 44f when the water jet is jetted to the almen strip 50. Therefore, deformation of the almen strip 50 due to the inflow of the water jet to between the almen strip 50 and the support surface 44a is further suppressed. As a result, the plastic deformation of the almen strip 50 by an action other than the water jet peening is suppressed, and more highly accurate evaluation of the compressive residual stress provided in the water jet peening can be performed.

An almen strip holding portion 44 illustrated in FIGS. 17 and 18 allows the plate surface of the almen strip 50 to be in contact with and attached to the support surface 44a, and includes the fixing members 44d as the attaching portions, as described above. The support surface 44a of the almen strip holding portion 44 has an area broader than the effective range where the water jet acts. The fixing members 44d are configured as bolts, includes the pressing surface 44e abutting on the outer edge of the almen strip 50, and fix the almen strip 50 to the support surface 44a (the upper surface of the support plate 40a in the water jet peening compressive residual stress test device 4). The almen strip 50 illustrated in FIGS. 17 and 18 is a rectangular plate member formed to have the plate thickness of about 1 to 2 mm, and has an area broader than the effective range 163c where the water jet acts. The fixing members 44d abut on the outer edge of the almen strip 50, and thus suppress the vicinity of the almen strip 50, spacing an area broader than the effective range 163c.

An almen strip holding portion 44 illustrated in FIGS. 17 and 18 is arranged to be positioned directly under the jet port mounting portion 41 in the water jet peening compressive residual stress test device 4. Then, the water jet is jetted through the jet port 163b mounted to the jet port mounting portion 41 to the portion of the effective range 163c of the almen strip 50, so that the water jet peening is applied to the portion. The effective range 163c where the water jet acts, of the almen strip 50 subjected to the water jet peening, is plastically deformed. Therefore, the degree and the size of a result of providing compressive residual stress provided in the water jet peening can be confirmed by measurement of the plastic deformation of the almen strip 50.

As described above, in the almen strip holding portion 44 of the water jet peening compressive residual stress test device 4 of the present embodiment, the support surface 44a has an area broader than the effective range 163c where the water jet acts, and the attaching portions (fixing members 44d) allow the almen strip 50 to be attached, spacing an area broader than the effective range 163c. Therefore, the water jet peening is applied to the portion of the effective range 163c of the almen strip 50. Then, when the water jet is jetted to the almen strip 50, the inflow of the water jet to the portion not let out through the through hole 44c, and the portion between the almen strip 50 and the support surface 44a is suppressed. As a result, the plastic deformation of the almen strip 50 by an action other than the water jet peening can be suppressed, and more highly accurate evaluation of the compressive residual stress provided in the water jet peening can be performed.

FIGS. 19 and 20 illustrate an embodiment including a block portion 46A that blocks a space between the almen strip holding portion 44 and the jet port mounting portion 41. The block portion 46A is formed into a plate shape, and has a size to cover the almen strip holding portion 44. Further, it is favorable that the block portion 46A is provided in a movable manner between a position to release the space between the almen strip holding portion 44 and the jet port mounting portion 41, and a position to block the space between the almen strip holding portion 44 and the jet port mounting portion 41, as illustrated by the solid lines in FIGS. 19 and 20. An opening/closing mechanism 46B that opens/closes and moves the block portion 46A is provided with block portion 46A through sliders 46Bb slid and moved on fixed slide rails 46Ba, and moves the block portion 46A with an actuator (pneumatic cylinder or the like) 46Bc. Note that, in FIGS. 19 and 20, the almen strip holding portion 44 is the embodiment illustrated in FIGS. 13 and 14. However, the almen strip holding portion 44 is not limited to the embodiment.

As described above, the water jet peening compressive residual stress test device 4 of the present embodiment includes the block portion 46A that blocks the space between the almen strip holding portion 44 and the jet port mounting portion 41, and the opening/closing mechanism 46B that moves the block portion 46A to open/close the space between the almen strip holding portion 44 and the jet port mounting portion 41. Further, the space between the almen strip holding portion 44 and the jet port mounting portion 41 is blocked with the block portion 46A moved by the opening/closing mechanism 46B, and the water jet to the almen strip 50 is controlled until the water jet jetted through the jet port 163*b* is stabilized to a jet condition in which the water jet peening is carried out. Further, the space between the almen strip holding portion 44 and the jet port mounting portion 41 is released with the block portion 46A moved by the opening/closing mechanism 46B, and the water jet is jetted to the almen strip 50 after the jet condition is stabilized. As a result, the almen strip 50 is plastically deformed in the stable jet condition. Therefore, more highly accurate evaluation of the compressive residual stress provided in the water jet peening can be performed.

Further, the water jet peening compressive residual stress test device 4 of the present embodiment slides and moves the jet port mounting portion 41 and the high-pressure water pipe mounting portion 42 in the direction perpendicular to the direction into which the jet port 163*b* mounted to the jet port mounting portion 41 faces, with the slide-moving mechanism 43. Therefore, the jet port 163*b* is retracted from a position above the almen strip holding portion 44 (almen strip 50) until the water jet jetted through the jet port 163*b* is stabilized to the jet condition in which the water jet peening is carried out, and the jet port 163*b* is moved to the position above the almen strip holding portion 44 (almen strip 50), and the water jet is jetted to the almen strip 50 after the jet condition is stabilized. As a result, the almen strip 50 is plastically deformed in the stable jet condition. Therefore, more highly accurate evaluation of the compressive residual stress provided in the water jet peening can be performed.

In FIGS. 21 and 22, a test piece holding portion 47 is included, which holds a residual stress measurement test piece 51 that causes residual stress. The residual stress measurement test piece 51 is a rectangular plate member not plastically deformed by an action of the water jet, formed to have the plate thickness of about 10 mm, and having an area broader than the effective range 163*c* where the water jet acts. The test piece holding portion 47 is provided in parallel to the almen strip holding portion 44, and includes a support surface 44*a*, and attaching portions (a pressing member 44*b* and fixing members 44*d*), similarly to the almen strip holding portion 44. Further, the test piece holding portion 47 includes a recessed portion 44*f*, similarly to the almen strip holding portion 44. Further, the test piece holding portion 47 may be an embodiment in which the attaching portions are configured from the fixing members 44*d*, similarly to the almen strip holding portion 44 illustrated in FIGS. 17 and 18. Further, while the test piece holding portion 47 is integrally configured with the almen strip holding portion 44 in FIGS. 21 and 22, the test piece holding portion 47 may be separately configured from the almen strip holding portion 44. Note that, in FIGS. 21 and 22, the almen strip holding portion 44 is the embodiment illustrated in FIGS. 13 and 14. However, the almen strip holding portion 44 is not limited to the embodiment.

The almen strip holding portion 44 illustrated in FIGS. 21 and 22 is arranged to be positioned directly under the jet port mounting portion 41 in the water jet peening compressive residual stress test device 4. Then, the water jet is jetted through the jet port 163*b* mounted to the jet port mounting portion 41 to the portion of the almen strip 50 let out through the through hole 44*c*, so that the water jet peening is applied to the portion. The effective range 163*c* where the water jet acts, of the almen strip 50 subjected to the water jet peening, is plastically deformed. Therefore, the degree and the size of a result of providing compressive residual stress provided in the water jet peening can be confirmed by measurement of the plastic deformation of the almen strip 50. Further, the test piece holding portion 47 illustrated in FIGS. 21 and 22 slides and moves the jet port 163*b* with the slide-moving mechanism 43 to be positioned directly under the jet port mounting portion 41. Then, the water jet is jetted through the jet port 163*b* mounted to the jet port mounting portion 41 to the residual stress measurement test piece 51, so that the water jet peening is applied to the portion. The compressive residual stress is caused in the effective range 163*c* where the water jet acts, of the residual stress measurement test piece 51 subjected to the water jet peening. Therefore, the compressive residual stress provided in the water jet peening can be directly confirmed by measurement of the compressive residual stress of the residual stress measurement test piece 51.

As described above, the water jet peening compressive residual stress test device 4 of the present embodiment includes the test piece holding portion 47 that holds the residual stress measurement test piece 51 that causes residual stress, in parallel to the almen strip holding portion 44, thereby to confirm the compressive residual stress provided in the water jet peening by comparing the almen strip 50 and the residual stress measurement test piece 51.

REFERENCE SIGNS LIST

1 Water jet peening compressive residual stress test facility
2 Water tank
2*a* Water tank cover
2*b* Bottom surface
3 High-pressure water pump
4 Water jet peening compressive residual stress test device
40 Device main body
41 Jet port mounting portion
42 High-pressure water pipe mounting portion
43 Slide-moving mechanism
44 Almen strip holding portion
44*a* Support surface
44*b* Pressing member (attaching portion)
44*c* Through hole
44*d* Fixing member (attaching portion)

44*e* Pressing surface
44*f* Recessed portion
45 Mounting base
45*a* Through hole
46 Block portion
47 Test piece holding portion
5 Pressurizing means
6 High-pressure water supply pipe
50 Almen strip
51 Residual stress measurement test piece
163 Jet nozzle
163*b* Jet port
163*c* Effective range

The invention claimed is:

1. A water jet peening compressive residual stress test method comprising:

holding a plastically deformable Almen strip in a predetermined underwater environment; and jetting water jet to the Almen strip, wherein the water jet peening compressive residual stress test method is performed in a water jet peening compressive residual stress test facility comprising:

a water tank that creates the predetermined underwater environment;

a high-pressure water supply pipe configured to supply high-pressure water;

a high-pressure water pump configured to send the high-pressure water to the high-pressure water supply pipe; and a water jet peening compressive residual stress test device arranged in the underwater environment of the water tank and connected to the high-pressure water pump via the high-pressure water supply pipe, wherein the water jet peening compressive residual stress test device comprises:

a jet port mounting portion to which a jet port is mounted, the jet port being configured to jet the water jet;

a high-pressure water pipe mounting portion provided communicating into the jet port mounting portion, and to which the high-pressure water supply pipe is mounted; and an Almen strip holding portion including a support surface facing the jet port mounting portion, and an attaching portion configured to allow a plate surface of the plastically deformable plate-like Almen strip to be in contact with and attached to the support surface, wherein the attaching portion includes:

a pressing member including a through hole through which a portion of the Almen strip, to which the water jet is configured to be jetted, is exposed, and a pressing surface configured to abut on an outer edge of the Almen strip; and a fixing member configured to fix the pressing member to sandwich the Almen strip between the pressing surface of the pressing member and the support surface of the Almen strip holding portion, wherein a recessed portion configured to allow the Almen strip to be inserted to surround whole circumference of the Almen strip which is provided in at least one of the support surface of the Almen strip holding portion and the pressing surface of the pressing member.

2. The water jet peening compressive residual stress test method according to claim 1, further comprising:

providing the underwater environment by putting water in the water tank to be sealed and pressurizing the sealed water tank.

3. A water jet peening compressive residual stress test device comprising:

a jet port mounting portion to which a jet port is mounted, the jet port jetting water jet;

a high-pressure water pipe mounting portion provided communicating into the jet port mounting portion, and to which a high-pressure water supply pipe is mounted, the high-pressure water supply pipe supplying high-pressure water; and an Almen strip holding portion including a support surface facing the jet port mounting portion, and an attaching portion configured to allow a plate surface of a plastically deformable plate-like Almen strip to be in contact with and attached to the support surface, wherein the attaching portion includes:

a pressing member including a through hole through which a portion of the Almen strip, to which the water jet is configured to be jetted, is exposed, and a pressing surface configured to abut on an outer edge of the Almen strip; and a fixing member configured to fix the pressing member to sandwich the Almen strip between the pressing surface of the pressing member and the support surface of the Almen strip holding portion, wherein a recessed portion configured to allow the Almen strip to be inserted to surround whole circumference of the Almen strip which is provided in at least one of the support surface of the Almen strip holding portion and the pressing surface of the pressing member.

4. The water jet peening compressive residual stress test device according to claim 3, wherein the support surface except areas on which the attaching portion is attached has an area broader than an effective range where the water jet acts, and the attaching portion allows the Almen strip to be attached.

5. The water jet peening compressive residual stress test device according to claim 3, further comprising:

a test piece holding portion provided in parallel to the Almen strip holding portion, and configured to hold a test piece that produces residual stress with the water jet.

6. The water jet peening compressive residual stress test device according to claim 3, further comprising:

a block portion configured to block a space between the Almen strip holding portion and the jet port mounting portion; and an opening/closing mechanism configured to move the block portion to open/close the space between the Almen strip holding portion and the jet port mounting portion.

7. The water jet peening compressive residual stress test device according to claim 3, further comprising:

a slide-moving mechanism configured to slide and move the jet port mounting portion and the high-pressure water pipe mounting portion in a direction perpendicular to a direction into which the jet port mounted to the jet port mounting portion faces.

8. A water jet peening compressive residual stress test facility comprising:

a water tank which creates a predetermined underwater environment; and a high-pressure water pump configured to send high-pressure water to the high-pressure water supply pipe that supplies the high-pressure water; and the water jet peening compressive residual stress test device according to claim 3 arranged in the underwater environment of the water tank and connected to the high-pressure water pump via the high-pressure water supply pipe.

9. The water jet peening compressive residual stress test facility according to claim 8, further comprising:

a sealing means configured to seal an inside of the water tank; and a pressurizing means configured to pressurize the inside of the sealed water tank.

* * * * *